United States Patent
Zeller et al.

(10) Patent No.: US 6,469,005 B1
(45) Date of Patent: Oct. 22, 2002

(54) PROPARGYLETHER DERIVATIVES

(75) Inventors: Martin Zeller, Baden; André Jeanguenat, Basel, both of (CH); Clemens Lamberth, Efringen-Kirchen (DE); Walter Kunz, Oberwil (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/903,651

(22) Filed: Jul. 11, 2001

Related U.S. Application Data

(63) Continuation of application No. PCT/EP00/00106, filed on Jan. 10, 2000.

(30) Foreign Application Priority Data

Jan. 11, 1999 (GB) .............................................. 9900455

(51) Int. Cl.$^7$ .......................... A01N 43/58; C07C 213/00
(52) U.S. Cl. .......................... 514/248; 514/247; 564/79; 564/80; 564/97; 564/381
(58) Field of Search ................................ 514/248, 247; 564/79, 80, 97, 381

(56) References Cited

U.S. PATENT DOCUMENTS 6,130,251 A    10/2000  Seitz et al.

FOREIGN PATENT DOCUMENTS

| WO | WO 9429267 |   | 12/1994 |          |
|----|------------|---|---------|----------|
| WO | WO 9530651 |   | 11/1995 |          |
| WO | WO 97/14677 | * | 4/1997 | 564/79   |
| WO | WO 98/38161 | * | 9/1998 | 514/248  |

* cited by examiner

Primary Examiner—Alan L. Rotman
Assistant Examiner—Hector M Reyes
(74) Attorney, Agent, or Firm—William A. Teoli, Jr.; Thomas Hamilton

(57) ABSTRACT

Propargylether derivatives of formula I

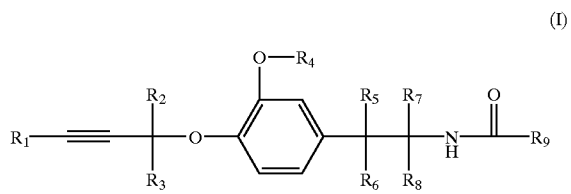

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl and $R_9$ is a group

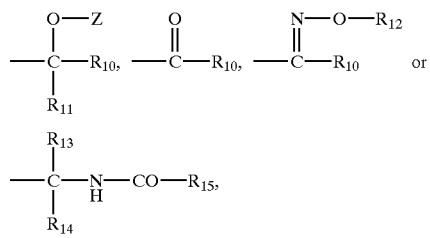

$R_{10}$ is optionally substituted aryl or optionally substituted heteroaryl, $R_{11}$ is hydrogen or optionally substituted alkyl, alkenyl or alkynyl, Z is hydrogen —CO—$R_{16}$, —COO$R_{16}$, —CO—COO$R_{16}$ or —CON$R_{16}R_{17}$, $R_{12}$ is hydrogen, or optionally substituted alkyl, alkenyl or alkynyl, $R_{13}$ is hydrogen or alkyl, $R_{14}$ is hydrogen, alkyl, cycloalkyl or cycloalkyl-alkyl, $R_{15}$ is alkyl, alkenyl, alkynyl, optionally substituted aryl or optionally substituted aryl-alkyl, and $R_{16}$ and $R_{17}$ are independently of each other hydrogen, optionally substituted alkyl, optionally substituted cycloalkyl, optionally substituted aryl or optionally substituted heteroaryl, have been found to be useful for controlling or preventing the infestation of plants by phytopathogenic microorganisms, especially fungi.

The invention relates the novel compounds and also to the preparation thereof and to the use of the compounds for plant protection, and to compositions suitable for applying the novel compounds in agricultural techniques.

14 Claims, No Drawings

PROPARGYLETHER DERIVATIVES

This application is a continuation of international application no. PCT/EP00/00106 filed Jan. 10, 2000 which is fully incorporated by reference herein.

The present invention relates to novel propargylether derivatives of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to propargylether derivatives of the general formula I

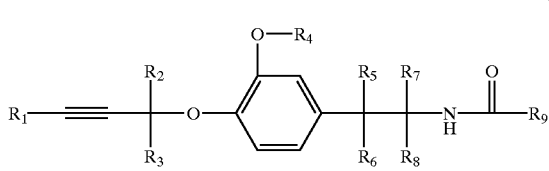

(I)

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl and

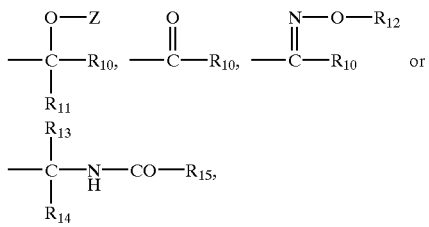

$R_{10}$ is optionally substituted aryl or optionally substituted heteroaryl, $R_{11}$ is hydrogen or optionally substituted alkyl, alkenyl or alkynyl, Z is hydrogen —CO—$R_{16}$, —COO$R_{16}$, —CO—COO$R_{16}$ or —CONR$_{16}$R$_{17}$, $R_{12}$ is hydrogen, or optionally substituted alkyl, alkenyl or alkynyl, $R_{13}$ is hydrogen or alkyl, $R_{14}$ is hydrogen, alkyl, cycloalkyl or cycloalkyl-alkyl, $R_{15}$ is alkyl, alkenyl, alkynyl, optionally substituted aryl or optionally substituted aryl-alkyl, and $R_{16}$ and $R_{17}$ are independently of each other hydrogen, optionally substituted alkyl, optionally substituted cycloalkyl, optionally substituted aryl or optionally substituted heteroaryl.

In the above definition aryl includes aromatic hydrocarbon rings like phenyl, naphthyl, anthracenyl, phenanthrenyl and biphenyl like 1,3-biphenyl and 1,4-biphenyl, with phenyl being preferred.

Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may be optionally substituted. This means they may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl.

Optionally substituted alkyl, alkenyl, alkynyl or cycloalkyl groups may carry one or more substituents selected from halogen, alkyl, alkoxy, alkylthio, nitro, cyano, hydroxy, mercapto, alkylcarbonyl or alkoxycarbonyl. Preferably, the number of substituents is no more than three with the exception of halogen, where the alkyl groups may be perhalogenated.

In the above definitions "halogen" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2butynyl or octyn-1-yl.

A haloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, etc.

The presence of at least one asymmetric carbon atom in the compounds of formula I means that the compounds may occur in optically isomeric and enantiomeric forms. As a result of the presence of a possible aliphatic C=C double bond, geometric isomerism may also occur. Formula I is intended to include all those possible isomeric forms and mixtures thereof.

Preferred subgroups of compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl; or $R_1$ is hydrogen, $C_1$–$C_8$-alkyl, $C_3$–$C_8$-cycloalkyl, phenyl or naphthyl; phenyl and naphthyl being optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; or $R_1$ is hydrogen, $C_1$–$C_8$-alkyl, phenyl optionally substituted by one to three substituents selected from the group comprising $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen, cyano, nitro and $C_1$–$C_8$-alkoxycarbonyl; or $R_2$ and $R_3$ are hydrogen; or $R_4$ is alkyl; or $R_5$, $R_6$, and $R_7$ are hydrogen; or $R_8$ is $C_1$–$C_6$-alkyl; or $R_4$ is $C_1$–$C_6$-alkyl; or $R_8$ is methyl or ethyl; or $R_4$ is methyl or ethyl; or $R_{10}$ is aryl or heteroaryl, each optionally substituted by substituents selected from to group comprising alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; or $R_{10}$ is phenyl, naphthyl, 1,3-biphenyl or 1,4-biphenyl, each optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; or $R_{10}$ is phenyl, naphthyl, 1,3-biphenyl or 1,4-biphenyl, each optionally substituted by one to three substituents selected from the group comprising $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen, cyano, nitro and $C_1$–$C_8$-alkoxycarbonyl; or $R_{11}$ is hydrogen, $C_1$–$C_4$-alkyl, $C_1$–$C_4$-haloalkyl, $C_3$–$C_4$-alkenyl or $C_3$–$C_4$-alkynyl; or $R_{11}$ is hydrogen or $C_1$–$C_4$-alkyl; or $R_{11}$ is hydrogen; or Z is hydrogen or —CO—$R_{16}$ wherein $R_{16}$ is $C_1$–$C_4$-alkyl or $C_3$–$C_6$-cycloalkyl; or Z is hydrogen or —CO—$R_{16}$ wherein $R_{16}$ is $C_1$–$C_4$-alkyl; or Z is hydrogen or acetyl; or Z is hydrogen; or $R_{12}$ is hydrogen, $C_1$–$C_6$-alkyl, $C_1$–$C_6$-haloalkyl, $C_3$–$C_6$-alkenyl or $C_3$–$C_6$-alkynyl; or $R_{12}$ is hydrogen, $C_1$–$C_6$-alkyl, $C_3$–$C_6$-alkenyl or $C_3$–$C_6$-alkynyl; or $R_{12}$ is hydrogen or $C_1$–$C_3$-alkyl; or $R_{13}$ is hydrogen or $C_1$–$C_4$-alkyl; or $R_{13}$ is hydrogen; or $R_{14}$ is $C_1$–$C_6$-alkyl or $C_3$–$C_7$-cycloalkyl; or $R_{14}$ is $C_2$–$C_5$-alkyl or $C_3$–$C_7$-cycloalkyl; or $R_{15}$ is alkyl, alkenyl, alkynyl; aryl or aryl-alkyl wherein aryl and aryl-alkyl are each optionally substituted by substituents selected from the group comprising alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; or $R_{15}$ is $C_1$–$C_8$-alkyl, $C_3$–$C_8$-alkenyl, $C_3$–$C_8$-alkynyl; phenyl or benzyl wherein the phenyl and benzyl is optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; or $R_{15}$ is $C_3$–$C_6$-alkyl, $C_3$–$C_6$-alkenyl or phenyl optionally substituted by one to three substituents selected from the group comprising $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen and cyano.

One preferred subgroup of the compounds of formula I consists of those compounds wherein $R_{11}$ is hydrogen or alkyl, Z is hydrogen or —CO—$R_{16}$, $R_{12}$ is hydrogen, alkyl, alkenyl or alkynyl, and $R_{16}$ is hydrogen or alkyl.

Further preferred subgroups of the compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl; and $R_4$ is alkyl; and $R_{10}$ is aryl or heteroaryl, each optionally substituted by substituents selected from to group comprising alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; and Z is hydrogen or —CO—$R_{16}$ wherein $R_{16}$ is $C_1$–$C_4$-alkyl; and $R_{15}$ is alkyl, alkenyl, alkynyl; aryl or aryl-alkyl wherein aryl and aryl-alkyl are each optionally substituted by substituents selected from the group comprising alkyl, alkenyl, alkynyl, cycloalkyl, cycloalkylalkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; or $R_1$ is hydrogen, $C_1$–$C_8$-alkyl, $C_3$–$C_8$-cycloalkyl, phenyl or naphthyl; phenyl and naphthyl being optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_2$, $R_3$, $R_5$, $R_6$, and $R_7$ are hydrogen; and $R_4$ and $R_8$ are independently $C_1$–$C_6$-alkyl; and $R_{10}$ is phenyl, naphthyl, 1,3-biphenyl or 1,4-biphenyl, each optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_{11}$ is hydrogen or $C_1$–$C_4$-alkyl; and Z is hydrogen or acetyl; and $R_{12}$ is hydrogen, $C_1$–$C_6$-alkyl, $C_3$–$C_6$-alkenyl or $C_3$–$C_6$-alkynyl; and $R_{13}$ is hydrogen or $C_1$–$C_4$-alkyl; and $R_{14}$ is $C_1$–$C_6$-alkyl or $C_3$–$C_7$-cycloalkyl; and $R_{15}$ is $C_1$–$C_8$-alkenyl, $C_3$–$C8$-alkynyl; phenyl or benzyl wherein the phenyl and benzyl is optionally substituted by one to three substituents selected from the group comprising $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; or $R_1$ is hydrogen, $C_1$–$C_8$-alkyl, phenyl optionally substituted by one to three substituents selected from the group comprising $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen, cyano, nitro and $C_1$–$C_8$-alkoxycarbonyl; and $R_2$, $R_3$, $R_5$, $R_6$, and $R_7$ are hydrogen; and $R_4$ and $R_8$ are each independently methyl or ethyl; and $R_{10}$ is phenyl, naphthyl, 1,3-biphenyl or 1,4-biphenyl, each optionally substituted by one to three substituents selected from the group comprising $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen, cyano, nitro and $C_1$–$C_8$-alkoxycarbonyl; and $R_{11}$, Z and $R_{13}$ are each hydrogen; and $R_{12}$ is hydrogen or $C_1$–$C_3$-alkyl; and $R_{14}$ is $C_2$–$C_5$-alkyl or $C_3$–$C_7$-cycloalkyl; and $R_{15}$ is $C_3$–$C_6$-alkyl, $C_3$–$C_6$-alkenyl or phenyl optionally substituted by one to three substituents selected from the group comprising $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen and cyano.

Preferred individual compounds are:

2-(3,4-dichloro-phenyl)-2-hydroxy-N-[2-(3-methoxy-4-prop-2-ynyloxy-phenyl)-ethyl]-acetamide,
2-(3,4-dichloro-phenyl)-2-hydroxy-N-[2-(3-methoxy-4-pent-2-ynyloxy-phenyl)-ethyl]-acetamide,
2-(4-fluoro-phenyl)-2-hydroxy-N-[2-(3- methoxy-4-prop-2-ynyloxy-phenyl)-ethyl]-acetamide,
2-(4-chloro-phenyl)-2-hydroxy-N-[2-(3-methoxy-4-prop-2-ynyloxy-phenyl)-ethyl]-acetamide,
2-(4-bromo-phenyl)-2-hydroxy-N-[2-(3-methoxy-4-prop-2-ynyloxy-phenyl)-ethyl]-acetamide,
2-(4-methoxy-phenyl)-2-hydroxy-N-[2-(3-methoxy-4-prop-2-ynyloxy-phenyl)-ethyl]-acetamide,
2-(4-methyl-phenyl)-2-hydroxy-N-[2-(3-methoxy-4-prop-2-ynyloxy-phenyl)-ethyl]-acetamide,
2-(2-naphthyl)-2-hydroxy-N-[2-(3-methoxy-4-prop-2-ynyloxy-phenyl)-ethyl]-acetamide,
2-(3,4-dichloro-phenyl)-N-[2-(3-methoxy-4-prop-2-ynyloxy-phenyl)-ethyl]-2-oxo-acetamide,
2-(3,4-dichloro-phenyl)-N-[2-(3-methoxy-4-pent-2-ynyloxy-phenyl)-ethyl]-2-oxo-acetamide,
2-(4-chloro-phenyl)-N-[2-(3-methoxy-4-prop-2-ynyloxy-phenyl)-ethyl]-2-oxo-acetamide,
2-(4-bromo-phenyl)-N-[2-(3-methoxy-4-prop-2-ynyloxy-phenyl)-ethyl]-2-oxo-acetamide,
2-(4-methyl-phenyl)-N-[2-(3-methoxy-4-prop-2-ynyloxy-phenyl)-ethyl]-2-oxo-acetamide,
2-(3,4-dimethoxy-phenyl)-N-[2-(3-methoxy-4-prop-2-ynyloxy-phenyl)-ethyl]-2-oxo-acetamide,
2-(1-methylethoxycarbonylamino)-N-[2-(3-methoxy-4-prop-2-ynyloxy-phenyl)-ethyl]-3-methylbutyramide,
2-(1,1-dimethylethoxycarbonylamino)-N-[2-(3-methoxy-4-prop-2-ynyloxy-phenyl)-ethyl]-3-methylbutyramide,
2-(1,1-dimethylethoxycarbonylamino)-N-{2-[3-methoxy-4-(pent-2-ynyloxy)-phenyl]-ethyl}-3-methylbutyramide,
2-(1,1-dimethylethoxycarbonylamino)-N-{2-[3-methoxy-4-(4-fluorophenylprop-2-ynyloxy)-phenyl]-ethyl}-3-methylbutyramide,
2-(1,1-dimethylethoxycarbonylamino)-N-{2-[3-methoxy-4-(4-chlorophenylprop-2-ynyloxy)-phenyl]-ethyl}-3-methylbutyramide,
2-(3,4-dichloro-phenyl)-N-[2-(3-methoxy-4-prop-2-ynyloxy-phenyl)-ethyl]-2-methoximino-acetamide,
2-(4-chloro-phenyl)-N-[2-(3-methoxy-4-prop-2-ynyloxy-phenyl)-ethyl]-2-methoximino-acetamide,
2-(4-methyl-phenyl)-N -[2-(3-methoxy-4-prop-2-ynyloxy-phenyl)-ethyl]-2-methoximino-acetamide,
2-(4-bromo-phenyl)-N-[2-(3-methoxy-4-prop-2-ynyloxy-phenyl)-ethyl]-2-methoximino-acetamide;
2-(4-chloro-phenyl)-2-hydroxy-N-[(R)2-(3-methoxy-4-prop-2-ynyloxy-phenyl)-propyl]-acetamide,
2-(4-chloro-phenyl)-2-hydroxy-N-[(S)2-(3-methoxy-4-prop-2-ynyloxy-phenyl)-propyl]-acetamide,
2-(4-chloro-2-nitro-phenyl)-2-hydroxy-N-[2-(3-methoxy-4-prop-2-ynyloxy-phenyl)-ethyl]-acetamide,
2-(4-ethyl-phenyl)-2-hydroxy-N-[2-(3-methoxy-4-prop-2-ynyloxy-phenyl)-ethyl]-acetamide,
2-(4-trifluoromethyl-phenyl)-2-hydroxy-N-[2-(3-methoxy-4-prop-2-ynyloxy-phenyl)-ethyl]-acetamide,
2-(4-methyl-phenyl)-2-hydroxy-N-[2-(3-methoxy-4-prop-2-ynyloxy-phenyl)-ethyl]-acetamide,
2-(4-chloro-phenyl)-2-hydroxy-N-[2-(3-methoxy-4-pent-2-ynyloxy-phenyl)-ethyl]-acetamide,
2-(4-bromo-phenyl)-2-hydroxy-N-[2-(3-methoxy-4-pent-2-ynyloxy-phenyl)-ethyl]-acetamide,
2-(4-methyl-phenyl)-2-hydroxy-N-[2-(3-methoxy-4-pent-2-ynyloxy-phenyl)-ethyl]-acetamide,
2(4-trifluoromethyl-phenyl)-2-hydroxy-N-[2-(3-methoxy-4-pent-2-ynyloxy-phenyl)-ethyl]-acetamide,
2-(4-chloro-phenyl)-2-hydroxy-N-[2-(3-methoxy-4-hex-2-ynyloxy-phenyl)-ethyl]-acetamide,
2-(4-bromo-phenyl)-2-hydroxy-N -[2-(3-methoxy-4-hex-2-ynyloxy-phenyl)-ethyl]-acetamide,
2-(4-methyl-phenyl)-2-hydroxy-N-[2-(3-methoxy-4-hex-2-ynyloxy-phenyl)-ethyl]-acetamide,
2-(3,4-dichloro-phenyl)-2-hydroxy-N-[2-(3-methoxy-4-hex-2-ynyloxy-phenyl)-ethyl]-acetamide, 2-naphthyl-2-hydroxy-N-[2-(3-methoxy-4-hex-2-ynyloxy-phenyl)-ethyl]-acetamide,
2-(4-trifluoromethyl-phenyl)-2-hydroxy-N-[2-(3-methoxy-4-hex-2-ynyloxy-phenyl)-ethyl]-acetamide,
2-(4-biphenyl)-2-hydroxy-N-[2-(3-methoxy-4-prop-2-ynyloxy-phenyl)-ethyl]-acetamide,
2-(4-bromo-phenyl)-2-methylalyloxy-N-[2-(3-methoxy-4-prop-2-ynyloxy-phenyl)-ethyl]-acetamide,
2-(4-chloro-phenyl)-2-hydroxy-2-(prop-2-ynyl)-N-[2-(3-methoxy-4-prop-2-ynyloxy-phenyl)-ethyl]-acetamide,
2-(3,4-dichloro-phenyl)-N-[2-(3-methoxy-4-pent-2-ynyloxy-phenyl)-ethyl]-2-oxo-acetamide,
2-(4-chloro-phenyl)-N-[2-(3-methoxy-4-prop-2-ynyloxy-phenyl)-ethyl]-2-methoxyimino-acetamide,
2-(4-methyl-phenyl)-N-[2-(3-methoxy-4-prop-2-ynyloxy-phenyl)-ethyl]-2-methoxyimino-acetamide, and
2-(3,4-dichloro-phenyl)-N-[2-(3-methoxy-4-prop-2-ynyloxy-phenyl)-ethyl]-2-methoxyimino-acetamide.

Certain amino acid carbamates, mandelic acid derivatives and alkoximino acetic acid derivatives have been proposed for controlling plant-destructive fungi (for example in EP-A-398072, WO 94/29267 and WO 96/23763). The action of those preparations is not, however, satisfactory in all aspects of agricultural needs. Surprisingly, with the compound structure of formula I, new kinds of microbicides having a high level of activity have been found.

The propargylether derivatives of formula I may be obtained according to one of the processes of Schemes 1 to 5:

mixed anhydrides, such as mixed anhydrides with O-alkylcarbonates, like activated esters, such as p-nitrophenylesters or N-hydroxysuccinimidesters, as well as in-situ-formed activated forms of the amino acid of formula II with condensating agents, such as dicyclohexylcarbodiimide, carbonyldiimidazole, benzotriazol-1-yloxy-tris(dimethylamino)phosphonium hexafluorophosphate, O-benzotriazol-1-yl N,N,N',N'-bis(pentamethylene)uronium hexafluorophosphate, O-benzotriazol-1-yl N,N,N',N'-bis(tetramethylene)uronium hexafluorophosphate, O-benzotriazol-1-yl N,N,N',N'-tetramethyluronium hexafluoro-phosphate or benzotriazol-1-yloxy-tripyrrolidinophosphonium hexafluorophosphate. The mixed anhydrides of the acids of the formula II may be prepared by reaction of an amino acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, N-methyl-piperidine or N-methyl-morpholine.

The present reaction is preferably performed in a solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitrites e.g. acetonitrile; or ethers e.g. diethylether, tert-butyl-methylether, dioxane or tetrahydro-furane or water. It is also possible to use mixtures of these solvents. The reaction is preformed optionally in the Scheme 1:

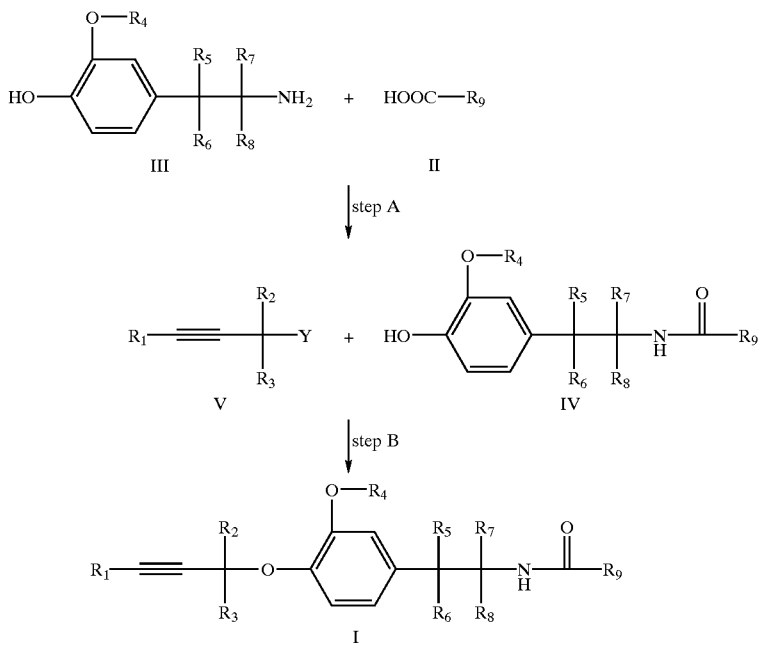

An acid of formula II or a carboxy-activated derivative of an acid of formula It wherein $R_9$ is as defined for formula I is reacted with an amine of formula III wherein $R_4$, $R_5$, $R_6$, $R_7$ and $R_8$ are as defined for formula I, optionally in the presence of a base and optionally in the presence of a diluting agent (step A).

Carboxy-activated derivatives of the acid of formula II are all compounds having an activated carboxyl group like an acid halide, such as an acid chloride, like symmetrical or presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

The compounds of formula I may then finally be prepared by reacting of a phenol of formula IV wherein $R_4$, $R_5$, $R_6$, $R_7$, $R_8$ and $R_9$ are as defined for formula I with a compound of formula V wherein $R_1$, $R_2$ and $R_3$ are as defined for formula I and wherein Y is a leaving group like a halide such as a chloride or bromide or a sulfonic ester such as a tosylate, mesylate or triflate (Step B).

The reaction is advantageously performed in a solvent like aromatic, non-aromatic or halogenated hydrocarbons, such as chlorohydrocarbons e.g. dichloromethane or toluene: ketones e.g. acetone or 2-butanone; esters e.g. ethyl acetate; ethers e.g. diethylether, tert-butyl-methylether, dioxane or tetrahydrofurane, amides e.g. dimethylformamide, nitriles e.g. acetonitrile, alcohols e.g. methanol, ethanol, isopropanol, n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

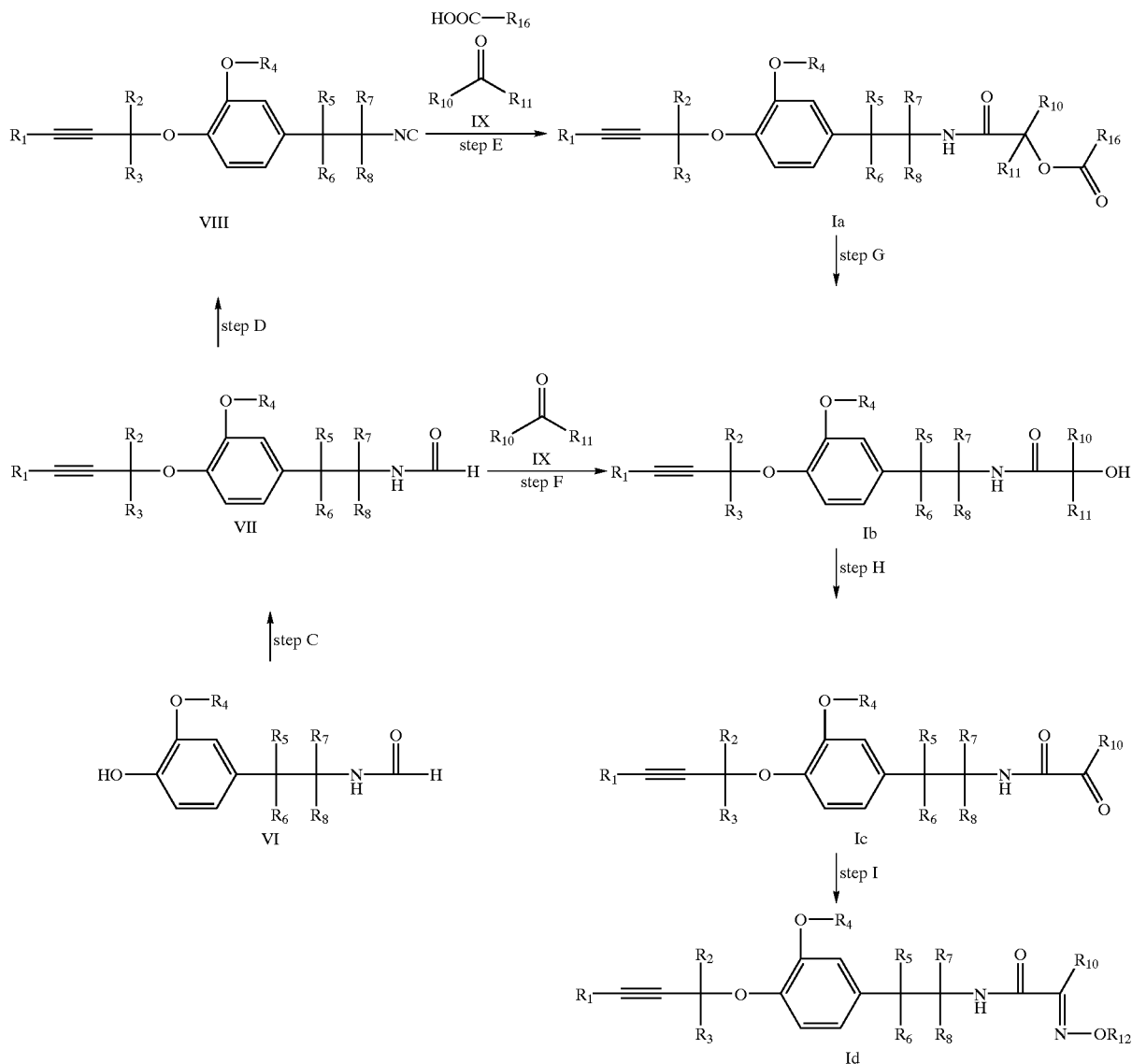

Step C: A compound of formula VI wherein $R_4$, $R_5$, $R_6$, $R_7$ and $R_8$ are as defined for formula I is alkylated with a compound of formula V (see Scheme 1) wherein $R_1$, $R_2$, $R_3$ and Y are as defined for Scheme 1 under the same conditions as defined for step B in Scheme 1.

Step D: A compound of formula VII wherein $R_1$, $R_2$, $R_3$, $R_4$, $R_5$, $R_6$, $R_7$ and $R_8$ are as defined for formula I is dehydrated to an isocyanide of formula VII wherein $R_1$, $R_2$, $R_3$, $R_4$, $R_5$, $R_6$, $R_7$ and $R_8$ are as defined for formula I under conditions known per se (D. Seebach, G. Adam, T. Gees, M. Schiess, W. Weigang, *Chem. Ber.* 1988, 121, 507).

Step E: An isocyanide of formula VII wherein $R_1$, $R_2$, $R_3$, $R_4$, $R_5$, $R_6$, $R_7$ and $R_8$ are as defined for formula I is reacted with an aldehyde or ketone of formula IX, wherein $R_{10}$ and $R_{11}$ are as defined for formula I in the presence of a carboxylic acid $R_{16}$—COOH wherein $R_{16}$ is hydrogen or lower alkyl, typically acetic acid, to give a O-acyl-α-hydroxy amide of formula Ia, wherein $R_1$, $R_2$, $R_3$, $R_4$, $R_5$, $R_6$, $R_7$, $R_8$, $R_{10}$ and $R_{11}$, are as defined for formula I, (a three-component Passerini Reaction, J. March, *Advanced Organic Chemistry*, 4th ed., Wiley, 1992, p. 980).

Alternatively an isocyanide of formula VIII wherein $R_1$, $R_2$, $R_3$, $R_4$, $R_5$, $R_6$, $R_7$ and $R_8$ are as defined for formula I is reacted with an aldehyde or ketone of formula IX in the presence of titanium tetrachloride to give an α-hydroxy amide of the formula Ib (where $R_1$, $R_2$, $R_3$, $R_4$, $R_5$, $R_6$, $R_7$, $R_8$, $R_{10}$ and $R_{11}$ have the same meaning as defined above) under conditions known per se (*Chem. Ber.* 1988, 121, 507; O. Ort et al. *Pesticide Sci.* 1997, 50, 331).

Step F: A compound of formula VII, wherein $R_1$, $R_2$, $R_3$, $R_4$, $R_5$, $R_6$, $R_7$ and $R_8$ are as defined for formula I is treated with one phosgene equivalent (e.g. triphosgene) and a base (e.g. triethylamine) and in a second step, without isolation of the isocyanide intermediate, is further treated with titanium tetrachloride and an aldehyde or ketone of formula IX, wherein $R_{10}$ and $R_{11}$ as defined for formula I under conditions known per se (WO 96/17840) to give an α-hydroxy amide of the formula Ib, wherein $R_1$, $R_2$, $R_3$, $R_4$, $R_5$, $R_6$, $R_7$, $R_8$, $R_{10}$ and $R_{11}$, are as defined for formula I.

Step G: An O-acyl-α-hydroxy amide of formula Ia wherein $R_1$, $R_2$, $R_3$, $R_4$, $R_5$, $R_6$, $R_7$, $R_8$, $R_{10}$, $R_{11}$ and $R_{16}$ are as defined above is hydrolyzed to a an α-hydroxy amide of formula Ib, wherein $R_1$, $R_2$, $R_3$, $R_4$, $R_5$, $R_6$, $R_7$, $R_8$, $R_{10}$ and $R_{11}$, are as defined for formula I under classical conditions (J. March, *Advanced Organic Chemistry*, 4th ed., Wiley, 1992).

Step H: A compound of formula Ib wherein $R_1$, $R_2$, $R_3$, $R_4$, $R_5$, $R_6$, $R_7$, $R_8$, $R_{10}$ and $R_{11}$, are as defined for formula I is oxidized by an organic oxidizing agent, e.g. an alkyl hydroperoxide, a DMSO-based reagent (T. T. Tidwell, *Org. React.*, 1990, 39, 297–572), an hypervalent iodine reagent, a dioxirane, a nitroxyl radical; or an inorganic oxidizing agent, e.g. peroxides, hypochlorites, transition metal oxide (e.g. Cr, Mn, Ru, Re, Os), sodium percarbonate, sodium perborate, silver carbonate.

The reaction of the compound of formula Ib with the oxidizing agent advantageously takes place in an inert solvent, such as THF, dichloromethane, water or a ketone, e.g. acetone, or in a mixture thereof, in the absence or in the presence of an acid or in the presence or in the absence of a base, at temperatures between –80° C. to +150° C.

Step I: A compound of formula Ic wherein $R_1$, $R_2$, $R_3$, $R_4$, $R_5$, $R_6$, $R_7$, $R_8$ and $R_{10}$ are as for formula I is reacted with $R_{12}$—O—$NH_2$ wherein $R_{12}$ is as defined above, under classical oximation conditions (e.g. J. March, *Advanced Organic Chemistry*, 4th ed., Wiley, 1992) to give a compound of formula Id wherein $R_1$, $R_2$, $R_3$, $R_4$, $R_5$, $R_6$, $R_7$, $R_8$, $R_{10}$ and $R_{12}$ are a defined above. Furthermore, when $R_{12}$ is H, compounds of formula Id may be alkylated with $R_{12}$—LG wherein $R_{12}$ is as defined above (with the exception of H), LG is a leaving group, typically Cl, Br, O-tosyl, O-mesyl, in the presence of a base in an inert solvent and at temperature between –20° C. to +160° C.

Scheme 3:
Preparation of compounds of formula Ie:

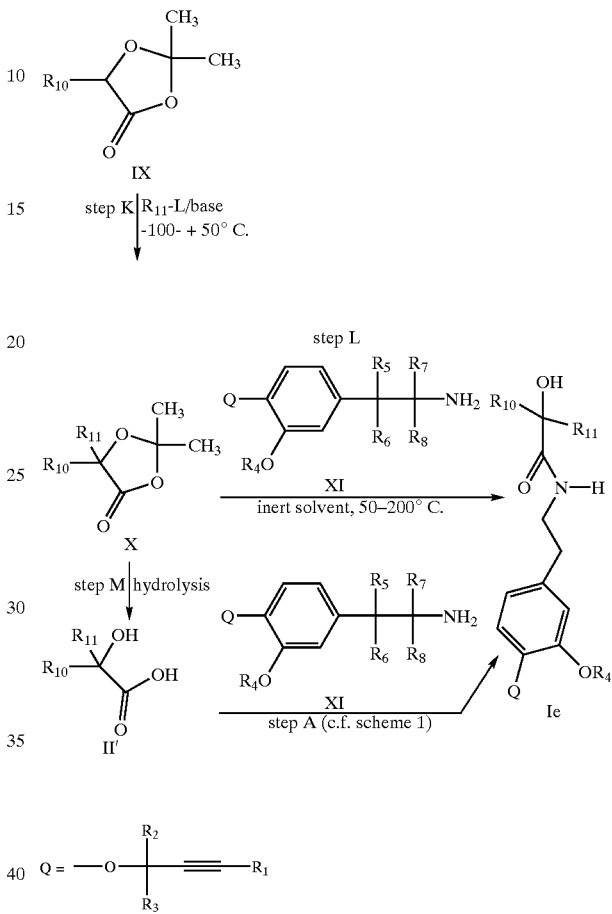

Step K: A dioxolanone IX (obtained by the condensation of a mandelic acid with acetone under acid catalysis (see EP-A-071568)) is subsequently treated with a base such as lithium disoproppylamide (LDA) and an alkylating agent $R_{11}$—L according to known procedures (THL 1994, 2891, Rec. Trav. Chim. Pays-Bas, DE 4319887).

Steps L and M: The resulting dioxolanone X is either heated with the appropriate amine XI at temperatures in between 50–200° C. (step L), or the dioxolanone is first hydrolysed in aqueous diluted mineral acid (e.g. HCl) or under basic conditions (aqueous sodium hydroxide (0–120° C.; step M) to the substituted hydroxy acid II' which then can be amidated (according to step A of scheme 1). Hydroxy acids II' can also be obtained by reaction of a Grignard reagent $R_{10}$—HgHal (starting from a aryl-halide and Mg) with an appropriate α-keto acid ester (Synthesis 1993, 606).

Scheme 4:
Further routes to intermediates and final products

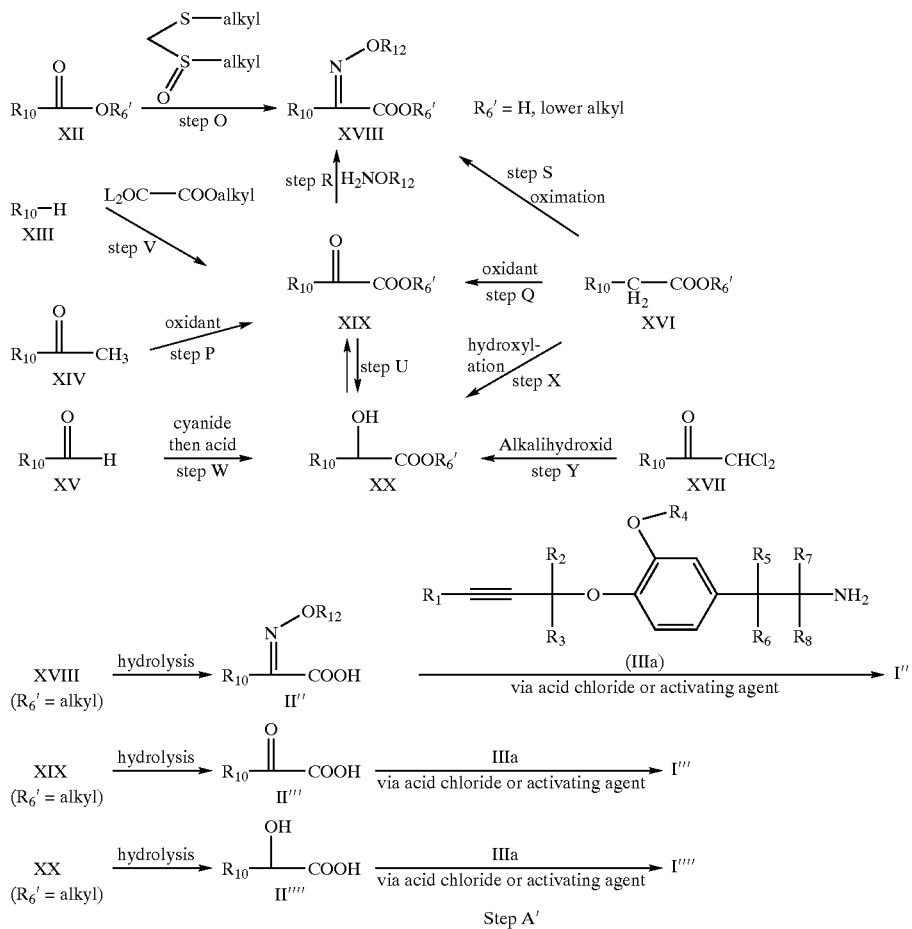

Step A'

Step O: An appropriate carboxylic acid ester derivative XII is reacted with a alkyl-methylsulfinyl-alkylsulfide (MMTS) in presence of a base to an intermediate which can be oxidized (NaIO$_4$) to a keto-thiomethylester which can be oximated to an oximino-carboxylic acid XVIII as described in J.Med. Chem. 28,1896.

Step P. Step Q: An acetophenone derivative XIV or a phenyl acetic acid derivative XVI are oxidized to an keto-carboxylic acid derivative XIX with an oxidant e.g. SeO$_2$ in a inert solvent as dioxane, pyridine at temperatures between 20–150° C. (J. Gen. Org. Chem. USSR, 21, 694 (1951)

Step R: A keto-carboxylic acid derivative XIX is transformed with a hydroxylamine derivative H$_2$NOR$_{12}$ in inert a solvent according to step I (see scheme 2) to the corresponding oxime XVIII.

Step S: An aryl acetic acid ester XVI derivative is oximated with an alkyl nitrite under basic or acid conditions as described in Org. reactions Vol.7, 327 (1953); Houben Weyl X/1, 911 ff; ibid. X/4, 44 ff.

Step U: A keto-carboxylic acid derivative XIX is reduced either with hydrogen in presence of a catalyst such as PtO$_2$ in a inert solvent like tetrahydrofurane, or with sodium borohydride at low temperature (−20° C. to +60° C.) in a solvent such as an alcohol (ethanol) or a cyclic ether to the mandelic acid derivative XX. A series of chiral catalysts is described in the literature in order to obtain enantiomerically pure alcohols (Org. Synth. 63, 18 (1984; JACS 109, 5856; C. R. Stephenson, Advanced Asymm.Synthesis London 1996; M.Hudlicky. Reductions in Org. Chemistry, ACS Monogr. 188, Washington 1996)

If desired, the alcohol XX may be oxidized with an oxidant (e.g. DMSO/ClCOCOCl/tert.amine; J. Am. Chem. Soc. 108,1035) to the ketone XIX as described for step H (see scheme 2), (M.Hudlicky, Oxidations in Org. Chemistry, ACS Monograph 186, Washington, 1990)

Step V: An aryl derivative XIII is transformed to a keto-carboxylic acid ester XIX by treating it with an oxalic ester derivative L$_2$OC—COOalkyl, where L$_2$ represents a leaving group such as a chlorine atom or an alkoxy radical, in presence of a Lewis acid e.g. AlCl$_3$ in a inert solvent such as dichlorobenzene or CS$_2$. (J Med. Chem. 28, 1896).

Step W: An aldehyde XV is transformed to the corresponding cyanohydrine by reaction with an alkali cyanide (e.g. KCN) in presence of a sodium hydrogen-sulfite (NaHSO$_3$) in an inert solvent such as water; or by reaction with a trialkyl-silylcyanide in presence of a Lewis acid (ZnI$_2$).The cyanohydrine or its trialkylsilylester is then hydrolysed in mineral acids such as aqueous hydrochloric acid as described in Org. Synth. Coll. Vol. V, 437 (1973).

Step X: An aryl acetic acid ester XVI is hydroxylated by reaction with a derivative of hydrogen peroxide, e.g. bist-rimethylsilylhydrogen peroxide in a inert solvent and in presence of a base such as lithium diisopropylamide (LDA) at temperatures between −90° C. to +50° C. as described in Synth. Comm. 18, 2141 (1988).

Step Y: A dichloro acetophenone XVII is treated with an alkali hydroxide (NaOH) in water as described in EP-A-071568.

Step A': Intermediates XVIII, XIX and XX, where $R_6'$ has the meaning of alkyl may be hydrolysed with 1.0 to 1.5 equivalents of aqueous alkali hydroxide in water or in mixtures with an alcohol or tetrahydrofurane leading to the corresponding acids (II", II''', II''''). The acids II", II''', II'''' may be reacted with the appropriate amine IIIa to obtain the amides I", I''' and I''''. The reaction may be directed either via acid chloride in presence of a base (pyridine or triethylamine) in an inert solvent or preferably directly in combination with an activating agent (e.g. dicyclohexyl carbodiimide, carbonyldiimidazole, or benzotriazole-1-yloxy-tris(dimethylamino) phosphonium hexafluorophosphate (BOP) in a inert solvent and optionally in presence of a base (tert. amine), according to M. Bodansky, Principles of Peptide Synthesis; M. Bodansky, The Practice of Peptide Synthesis, Springer-Verlag Berlin 1994) as indicated for step A (see scheme 1).

Intermediates XVIII, XIX and XX, where $R_6'$ stands for alkyl can also directly be reacted with an amine IIIa with or without a higher boiling solvent at temperatures in between 70–240° C. according to WO 94/29267.

propylamine or Buchwalds' ligand (2'-dicyclohexylphosphanyl-biphenyl-2-yl)-dimethylamine) and a palladium catalyst (e.g. $PdP(Ph)_4$, $Pd(OAc)_2$; $(PPh)_3PdCl_2$) in an inert solvent (benzene, toluene, acetonitrile, dioxane, water, aliphatic alcohols) at 0–150° C.

Step A: The resulting carboxylic acid derivative XXI is then amidated to If as described for step A (see scheme 1). Direct amidation of XXII leads to the final products Ia–If.

The compounds of formula I are oils or solids at room temperature and are distinguished by valuable microbicidal properties. They can be used in the agricultural sector or related fields preventively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy phytopatho- Scheme 5:
Bisaryl-intermediates XXI and further transformations

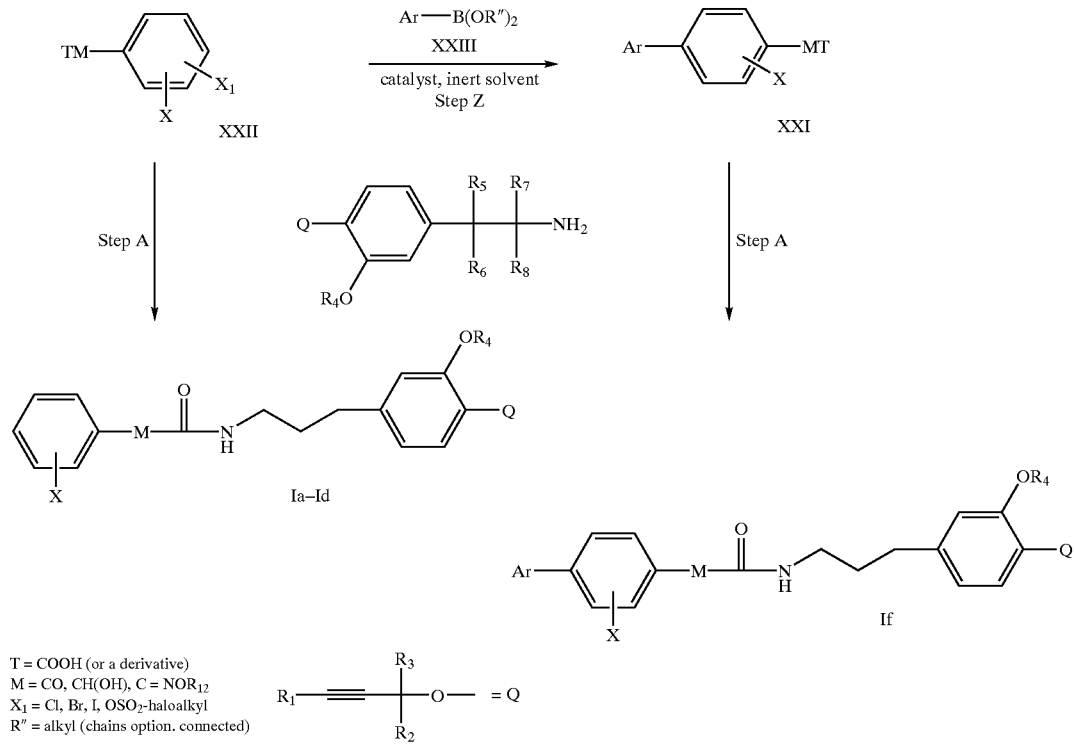

Step Z: A carboxylic acid derivative XXII having a leaving group XI is cross-coupled according to the Suzuki-methodology with an arylboronic acid or -ester XXIII to build a biphenyl derivative XXI (Synth. Comm.11, 513 (1981); Acta Chem. Scand. 47, 221; Chem. Rev. 95, 2457; Heterocycles 34, 1395) in presence of a base (alkali carbonate, alkali fluoride (e.g. CsF), tert. amine (ethyl diisogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class *Fungi imperfecti*

(e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities.

Mixing components which are particularly azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[a{[(a-methyl-3-trifluoromethylbenzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenyl-amino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), iprovalicarb (SZX 722).

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius. Ph stands for phenyl.

PREPARATION EXAMPLES
Example E1
2-(3,4-Dichloro-phenyl)-2-hydroxy-N-[2-(3-methoxy-4-prop-2-ynyloxy-phenyl)-ethyl]-acetamide

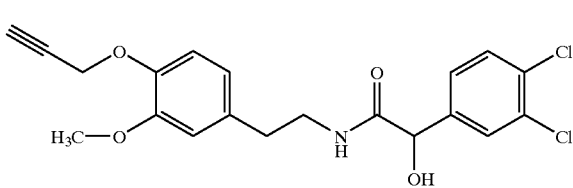

To a mixture of (3,4-dichloro-phenyl)-hydroxy-acetic acid (3 g), 4-(2-amino-ethyl)-2-methoxy-phenol hydrochloride (2.7 g) and ethyl-diisopropyl-amine (7 ml) in dimethylformamide (60 ml) is added benzotriazol-1-yloxytris(dimethylamino)phosphonium hexafluorophosphate (6 g) in one portion. The mixture is stirred at room temperature for 3 hours. Then water (400 ml) is added. The mixture is extracted with ethyl acetate (2×400 ml) and washed with brine (2×200 ml). The organic layers are collected, dried with $MgSO_4$ and evaporated. 2-(3,4-dichloro-phenyl)-2-hydroxy-N-[2-(4-hydroxy-3-methoxy-phenyl)-ethyl]-acetamide is obtained which is purified by flash column chromatography on silica gel (ethyl acetate/hexane 2:1); the product is an oil.

A mixture of 2-(3,4-dichloro-phenyl)-2-hydroxy-N-[2-(4-hydroxy-3-methoxy-phenyl)-ethyl]-acetamide, propargyl bromide (0.5 ml) and potassium carbonate (1.5 g) in dimethyl sulfoxide is stirred at +80° C. for 3 hours. The mixture is cooled to room temperature and water (150 ml) is added. The mixture is extracted with ethyl acetate (2×200 ml) and washed with brine (100 ml). The organic layers are collected, dried with $MgSO_4$ and evaporated. 2-(3,4-Dichloro-phenyl)-2-hydroxy-N-[2-(3-methoxy-4-prop-2-ynyloxy-phenyl)-ethyl]-acetamide is obtained which is purified by flash column chromatography on silica gel (ethyl acetate/hexane 2:1); the product is an oil.

According to the procedure of Examples E1 the compounds listed in table E1 are obtained.

TABLE E1

| No. | $R_1$ | $R_{10}$ | physical data |
|---|---|---|---|
| E1.01 | H | 3,4-$Cl_2$—Ph | oil |
| E1.02 | $C_2H_5$ | 3,4-$Cl_2$—Ph | oil |
| E1.03 | 4-Cl—Ph | 3,4-$Cl_2$—Ph | oil |
| E1.04 | H | 4-F—Ph | oil |
| E1.05 | H | 4-Cl—Ph | oil |
| E1.06 | H | 4-Br—Ph | oil |
| E1.07 | H | 4-$H_3$CO—Ph | oil |
| E1.08 | H | 4-$H_3$C—Ph | oil |
| E1.09 | 4-Cl—Ph | 4-$H_3$C—Ph | m.p. 111–112 |
| E1.10 | H | 3,4-$F_2$—Ph | oil |
| E1.11 | H | 3-$H_3$CO-4-(HC≡C—$CH_2$—O—)—Ph | oil |
| E1.12 | H | 3,4-$(H_3CO)_2$—Ph | oil |
| E1.13 | H | 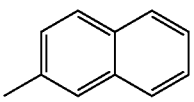 | m.p. 116–117 |

TABLE E1-continued

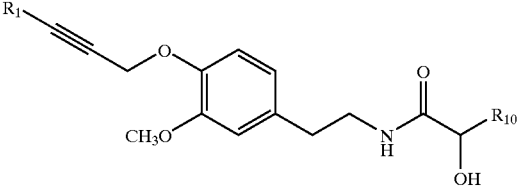

| No. | R₁ | R₁₀ | physical data |
|---|---|---|---|
| E1.14 | H | 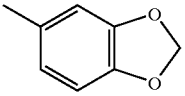 | oil |
| E1.15 | H | 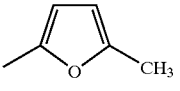 | oil |
| E1.16 | H | 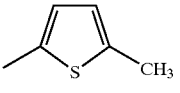 | oil |
| E1.17 | C₃H₇-i | 4-F—Ph | |
| E1.18 | C₃H₇-i | 4-Cl—Ph | |
| E1.19 | H | 4-Cl-2-NO₂—Ph | oil |
| E1.20 | H | 4-CH₃-4-NO₂—Ph | oil |
| E1.21 | H | 4-C₂H₅—Ph | oil |
| E1.22 | H | 4-C₃H₇-n-Ph | oil |
| E1.23 | H | 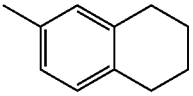 | oil |
| E1.24 | H | 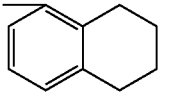 | oil |
| E1.25 | H | 4-C₃H₇-i-Ph | oil |
| E1.26 | H | 4-H₃CS—Ph | oil |
| E1.27 | C₂H₅ | 4-F—Ph | oil |
| E1.28 | C₂H₅ | 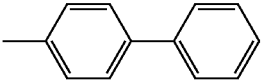 | oil |
| E1.29 | C₂H₅ | 4-C₂H₅—Ph | oil |
| E1.30 | H | 4-CF₃—Ph | oil |
| E1.31 | CH₃ | 4-Cl—Ph | oil |
| E1.32 | CH₃ | 4-Br—Ph | oil |
| E1.33 | CH₃ | 4-H₃C—Ph | resin |
| E1.34 | CH₃ | 4-H₃CO—Ph | resin |
| E1.35 | CH₃ | 3,4-F₂—Ph | oil |
| E1.36 | CH₃ | 3,4-Cl₂—Ph | oil |
| E1.37 | CH₃ | 3,4-(H₃CO)₂—Ph | resin |
| E1.38 | CH₃ | 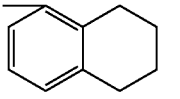 | oil |
| E1.39 | CH₃ | 4-CF₃—Ph | oil |
| E1.40 | C₂H₅ | 4-Cl—Ph | oil |
| E1.41 | C₂H₅ | 4-Br—Ph | oil |
| E1.42 | C₂H₅ | 4-H₃C—Ph | m.p. 101–103 |
| E1.43 | C₂H₅ | 4-H₃CO—Ph | oil |
| E1.44 | C₂H₅ | 3,4-F₂—Ph | oil |
| E1.45 | C₂H₅ | 3,4-(H₃CO)₂—Ph | oil |

TABLE E1-continued
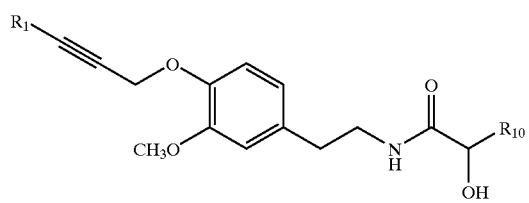
| No. | R₁ | R₁₀ | physical data |
|---|---|---|---|
| E1.46 | $C_2H_5$ | 4-CF₃—Ph | oil |
| E1.47 | $C_2H_5$ | 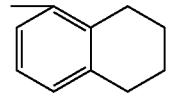 | oil |
| E1.48 | $C_3H_7$-n | 4-Cl—Ph | oil |
| E1.49 | $C_3H_7$-n | 4-Br—Ph | oil |
| E1.50 | $C_3H_7$-n | 4-H₃C—Ph | oil |
| E1.51 | $C_3H_7$-n | 4-H₃CO—Ph | oil |
| E1.52 | $C_3H_7$-n | 3,4-F₂—Ph | oil |
| E1.53 | $C_3H_7$-n | 3,4-Cl₂—Ph | oil |
| E1.54 | $C_3H_7$-n | 3,4-(H₃CO)₂—Ph | m.p. 95–97 |
| E1.55 | $C_3H_7$-n | 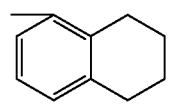 | m.p. 83–85 |
| E1.56 | $C_3H_7$-n | 4-CF₃—Ph | oil |
| E1.57 | H | 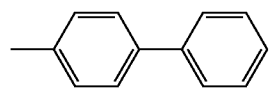 | viscous oil |
| E1.58 | H | 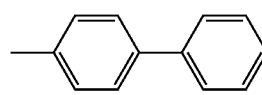 | m.p. 101–103 |
| E1.59 | H | 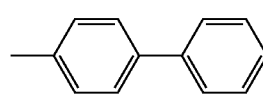 | m.p. 92–94 |
| E1.60 | H | 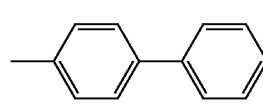 | m.p. 107–109 |
| E1.61 | H | 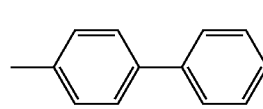 | m.p. 95–97 |
| E1.62 | H | 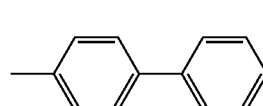 | |
| E1.63 | H |  | |
| E1.64 | H | 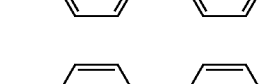 | |

TABLE E1-continued

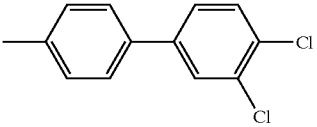

| No. | R₁ | R₁₀ | physical data |
|---|---|---|---|
| E1.65 | H | 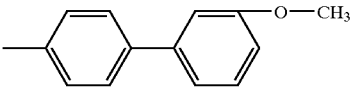 | |
| E1.66 | H | 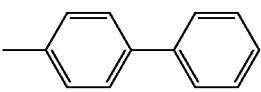 | |
| E1.67 | $C_2H_5$ | 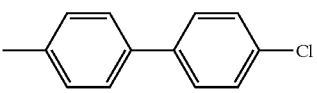 | |
| E1.68 | $C_2H_5$ | 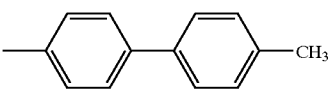 | |
| E1.69 | $C_2H_5$ | 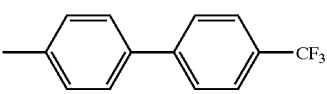 | |
| E1.70 | $C_2H_5$ | 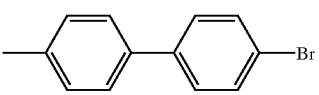 | |
| E1.71 | $C_2H_5$ | 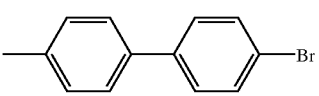 | |
| E1.72 | H | | |

TABLE Ea1

| No. | R₁ | R₁₀ | physical data |
|---|---|---|---|
| Ea1.01 | H | 4-Cl—Ph | oil (diastereomer 1) |
| Ea1.02 | H | 4-Cl—Ph | oil (diastereomer 2) |

Example E2

2-(3,4-Dichloro-phenyl)-2-methoxyimino-N-[2-(3-methoxy-4-prop-2-ynyloxy-Phenyl)-ethyl]-acetamide

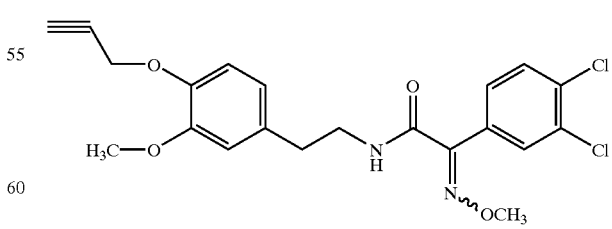

To a solution of 1.30 g (3.20 mmol) 2-(3,4-dichlorophenyl)-N-[2-(3-methoxy-4-prop-2-ynyloxy-phenyl)-ethyl]-2-oxo-acetamide in 7.0 ml ethanol, 0.52 ml pyridine (0.64 mmol) and 0.33 g (3.98 mmol)

O-methylhydroxylamine hydrochloride are added. The solution is heated at +80° C. for 4 hours. After evaporation of the solvent, the residue is submitted to flash-chromatography to yield the 2-(3,4-dichloro-phenyl)-2-methoxyimino-N-[2-(3-methoxy-4-prop-2-ynyloxy-phenyl)-ethyl]-acetamide as a white solid (m.p. 107–108° C.)

$^1$H-NMR (300 MHz, CDCl$_3$): 1.15 (t, 3H, CH$_2$CH$_3$), 2.22 (m, 2H, CH$_2$CH$_3$), 2.87 (t, 2H, CH$_2$CH$_2$), 3.64 (t, 2H, CH$_2$CH$_2$), 3.88 (s, 3H, OCH$_3$), 4.72 (m, 2H, OCH$_2$), 6.77 (m, 2H, CH arom.), 6.99 (d, 1H, CH arom.), 7.16 (t, 1H, NH), 7.57 (d, 8.22,m) and 8.49 (m, 3H, CH arom. ).

Example E3

2-(3,4-Dichloro-phenyl)-N-[2-(3-methoxy-4-pent-2-ynyloxy-phenyl)-ethyl]-2-oxo-acetamide

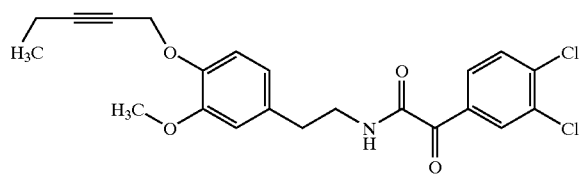

Example E4

2-(4'-Chloro-biphenyl-4-yl)-N-[2-(3-methoxy-4-prop-2-ynyloxy-phenyl)-ethyl]-2-oxo-acetamide

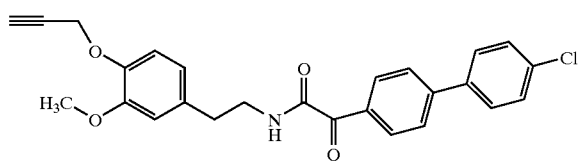

To a solution of 0.8 ml oxalyl chloride (9.0 mmol) in 8 ml methylenchloride at −63° C. is added in 15 minutes a solution of 0.84 ml DMSO (12.0 mmol) in 4 ml CH$_2$Cl$_2$. A solution of 2.6 g (6.0 mmol) of 2-(3,4-dichloro-phenyl)-2-hydroxy-N-[2-(3-methoxy-4-pent-2-ynyloxy-phenyl)-ethyl]-acetamide in 30 ml CH$_2$Cl$_2$ is added during 10 minutes. After 10 minutes at −65° C. a solution of 3.2 ml (24.0 mmol) triethylamine in 8 ml CH$_2$Cl$_2$ is added during 15 minutes. After another 15 minutes at the same temperature the mixture is hydrolysed with 6.0 ml water and allowed to warm up to room temperature. The solution is washed with solutions of KHSO$_4$ (20%), NaHCO$_3$ (saturated) and NaCl (saturated) After evaporation the residue is submitted to flash-chromatography (ethyl acetate 25, hexanes 75) to give the 2-(3,4-dichloro-phenyl)-N-[2-(3-methoxy-4-pent-2-ynyloxy-phenyl)-ethyl]-2-oxo-acetamide.

A mixture of 652 mg 2-(4'-chloro-biphenyl-4-yl)-2-oxo acetic acid, 1.5 g ethyldiisopropyl-amine and 1.25 g benzotriazole-1-yloxy-tris(dimethylamino) phosphonium hexafluoro-phosphate (BOP) in 15 ml dimethylformamide is stirred under cooling at 0° C. over night. The reaction mixture is then diluted with ethyl acetate, washed with water and brine, dried over sodium sulfate, evaporated and purified by HPLC (Lichrosphere Si-60/ethyl acetate-hexane) to obtain the desired 2-(4'-chloro-biphenyl-4-yl)-N-[2-(3-methoxy-4-prop-2-ynyloxy-phenyl)-ethyl]-2-oxo-acetamide, m.p. 122–124° C.

According to the procedures of Examples E2, E3 and E4 the compounds listed in table E2 are obtained.

TABLE E2

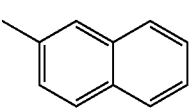

| No. | R$_1$ | X | R$_{10}$ | physical data |
|---|---|---|---|---|
| E2.01 | H | O | 3,4-Cl$_2$—Ph | m.p. 90–91 |
| E2.02 | C$_2$H$_5$ | O | 3,4-Cl$_2$—Ph | m.p. 94–95 |
| E2.03 | C$_2$H$_5$ | N—OCH$_3$ | 3,4-Cl$_2$—Ph | m.p. 107–108 |
| E2.04 | 4-Cl—Ph | O | 3,4-Cl$_2$—Ph | m.p. 142–143 |
| E2.05 | H | O | 4-F—Ph | oil |
| E2.06 | H | O | 4-Cl—Ph | m.p. 85–86 |
| E2.07 | H | N—OCH$_3$ | 4-Cl—Ph | m.p. 102–103 |
| E2.08 | H | O | 4-Br—Ph | m.p. 100–101 |
| E2.09 | H | O | 4-H$_3$C—Ph | m.p. 80–81 |
| E2.10 | H | N—OCH$_3$ | 4-H$_3$C—Ph | oil |
| E2.11 | 4-Cl—Ph | O | 4-H$_3$C—Ph | m.p. 128–129 |
| E2.12 | H | O | 3,4-F$_2$—Ph | m.p. 62–63 |
| E2.13 | H | O | 3-H$_3$CO-4-(HC≡C—CH$_2$—O)Ph | m.p. 86–87 |
| E2.14 | H | O | 3,4-(H$_3$CO)$_2$—Ph | m.p. 93–94 |
| E2.15 | H | O | 2-naphthyl | oil |

TABLE E2-continued

Structure: 4-(R₁-propargyloxy)-3-methoxyphenethyl-NH-C(=O)-C(=X)-R₁₀

| No. | R₁ | X | R₁₀ | physical data |
|---|---|---|---|---|
| E2.16 | H | O | 5-methyl-1,3-benzodioxole | m.p. 83–84 |
| E2.17 | H | N—OH | 4-Cl-2-NO₂—Ph | m.p. 131–132 (diastereomer A) |
| E2.18 | H | N—OH | 4-Cl-2-NO₂—Ph | oil (diastereomer B) |
| E2.19 | H | N—OH | 4-CH₃-2-NO₂—Ph | m.p. 144–145 |
| E2.20 | H | O | 4-Cl-2-NO₂—Ph | oil |
| E2.21 | H | O | 4-CH₃-2-NO₂—Ph | oil |
| E2.22 | H | O | 4-C₂H₅—Ph | oil |
| E2.23 | H | N—OCH₃ | 4-C₂H₅—Ph | oil |
| E2.24 | H | O | 6-methyl-1,2,3,4-tetrahydronaphthalene | oil |
| E2.25 | H | N—OCH₃ | 6-methyl-1,2,3,4-tetrahydronaphthalene | m.p. 41 |
| E2.26 | H | N—OCH₃ | 3,4-Cl₂—Ph | oil |
| E2.27 | H | N—OCH₃ | 4'-Cl-biphenyl-4-yl | m.p. 141–143 |
| E2.28 | H | O | 4'-Cl-biphenyl-4-yl | m.p. 122–124 |
| E2.29 | H | O | 4'-CH₃-biphenyl-4-yl | m.p. 126–128 |
| E2.30 | H | N—OCH₃ | 4'-CH₃-biphenyl-4-yl | m.p. 139–141 |
| E2.31 | H | N—OCH₃ | 4'-CF₃-biphenyl-4-yl | m.p. 128–130 |
| E2.32 | H | N—OCH₃ | biphenyl-4-yl | |
| E2.33 | H | O | 4'-Br-biphenyl-4-yl | m.p. 149–151 |

TABLE E2-continued

Structure: R₁-C≡C-CH₂-O-[phenyl with H₃CO]-CH₂CH₂-NH-C(=X)-C(=O)-R₁₀

| No. | R₁ | X | R₁₀ | physical data |
|---|---|---|---|---|
| E2.34 | H | N—OCH₃ | 4'-Br-biphenyl-4-yl | m.p. 151–153 |
| E2.35 | H | O | biphenyl-4-yl | |
| E2.36 | C₂H₅ | N—OCH₃ | 4'-Cl-biphenyl-4-yl | |
| E2.37 | C₂H₅ | O | 4'-Cl-biphenyl-4-yl | |
| E2.38 | C₂H₅ | O | 4'-CH₃-biphenyl-4-yl | |
| E2.39 | C₂H₅ | N—OCH₃ | 4'-CH₃-biphenyl-4-yl | |
| E2.40 | C₂H₅ | N—OCH₃ | 4'-CF₃-biphenyl-4-yl | |
| E2.41 | C₂H₅ | N—OCH₃ | biphenyl-4-yl | |
| E2.42 | C₂H₅ | O | 4'-Br-biphenyl-4-yl | oil |
| E2.43 | C₂H₅ | N—OCH₃ | 4'-Br-biphenyl-4-yl | |
| E2.44 | C₂H₅ | O | biphenyl-4-yl | |
| E2.45 | CH₃ | N—OCH₃ | 4'-Br-biphenyl-4-yl | |

Example E5

2-(3,4-Dichloro-phenyl)-2-hydroxy-N-[2-(3-methoxy-4-pent-2-ynyloxy-phenyl)-ethyl]-acetamide

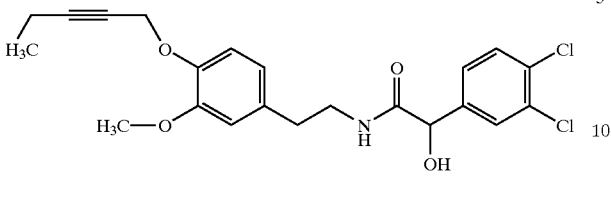

34 g (13.0 mmol) N-[2-(3-methoxy-4-pent-2-ynyloxy-phenyl)-ethyl]-formamide and 4.3 ml (32 mmol) triethylamine are dissolved in 13 ml $CH_2Cl_2$. 1.4 g (4.7 mmol) bis(trichloromethyl) carbonate (triphosgene) in 9 ml $CH_2Cl_2$ is added at +5° C. The mixture is stirred for 4 hours at +5° C. and then cooled to −78° C. A solution of 1.43 ml (13.0 mmol) $TiCl_4$ in 20 ml $CH_2Cl_2$ is added and the mixture is stirred for 2 hours at −40° C. 2.5 g (12.9 mmol) 3,4-dichlorobenzal-dehyde in 7 ml $CH_2Cl_2$ is added dropwise and the mixture is stirred for 17 h at room temperature. The mixture is hydrolysed with 7 ml HCl 5N, stirred 30 minutes at room temperature and washed with water. After evaporation the residue is submitted to flash-chromatography (ethyl acetate 6,hexanes 4) to give the 2-(3,4-dichloro-phenyl)-2-hydroxy-N-[2-(3-methoxy-4-pent-2-ynyloxy-phenyl)-ethyl]-acetamide.

$^1$H-NMR (300 MHz, $CDCl_3$): 1.15 (t, 3H, $CH_2CH_3$), 2.22 (m, 2H, $CH_2CH_3$), 2.75 (t, 2H, $CH_2CH_2$), 3.51 (m, 2H, $CH_2CH_2$), 3.69 (d, 2H, OH), 3.83 (s, 3H, $OCH_3$), 4.74 (m, 2H, OCH2), 4.96 (d, 1H, CHOH), 6.27 (t, 1H, NH), 6.58 (m, 1H), 6.68 (m, 1H), 6.92 (d, 1H), 7.19 (d, 1H), 7.42 (d, 1H) and 7.49 (m, 1H, CH arom.).

Example E6

2-(4'-Trifluoro-biphenyl-4-yl)-2-hydroxy-N-[2-(3-methoxy-4-prop-2-ynyloxy-phenyl)-ethyl]-acetamide

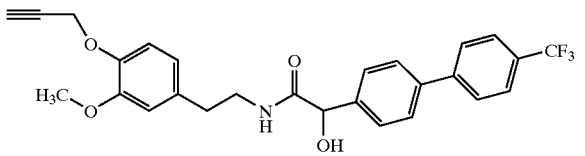

a) 4-(4-Trifluoromethyl)-acetophenone

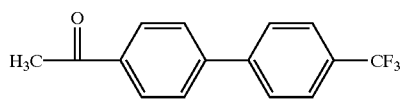

A suspension of 3.44 g 4-bromoacetophenone, 4.94 g 4-trifluoroboronic acid, 7.88 g cesiumfluoride, 80 mg palladium acetate and (2'-dicyclohexylphosphanyl-biphenyl-2-yl)-dimethyl-amine (Buchwalds' ligand), in 100 ml dioxane is heated under nitrogen. When the reaction is complete, the suspension is filtered over Hyflo, the filtrate is evaporated and purified by filtration over silicagel (hexane-ethyl acetate 7:3) to obtain 4-(4'-trifluoromethyl-phenyl)-acetophenone a yellowish solid, m.p. 114–116° C.

b) 2-(4'-Trifluoromethyl-biphenyl-4-yl)-2-oxo acetic acid

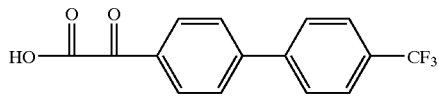

A mixture of 3.96 g of 4-(4'-trifluoromethyl-phenyl)-acetophenone and 3.9 g selenium dioxide in 21 ml pyridine is heated at 105° C. When the reaction is complete, the reaction is evaporated, dissolved in diethyl ether, made alkaline with dilute 1N sodium hydroxide and washed with diethyl ether. The aqueous layer is acidified with 1N HCl and extracted with dichloromethane. The extracts are washed with brine and dried over sodium sulfate. Evaporation leads to 2-(4'-trifluoromethyl-biphenyl-4-yl)-2-oxo acetic acid, m.p. 155° C. (decomp.).

c) 2-(4'-Trifluoro-biphenyl-4-yl)-2-hydroxy acetic acid

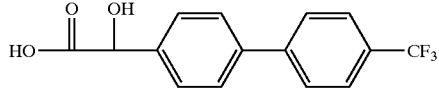

A solution of 1.47 g 2-(4'-trifluoro-biphenyl-4-yl)-2-oxo acetic acid in 20 ml tetrahydrofurane is hydrogenated at room temperature over 160 mg platinum(IV) oxide at low pressure until the hydrogen uptake is complete. The reaction mixture is filtered and evaporated to give the 2-(4'-trifluoro-biphenyl-4-yl)-2-hydroxy acetic acid , m.p. 185–187° C.

d) To a solution of 662 mg N-(2-(3-methoxy-4-prop-2-ynyloxy-phenyl)-ethylamine hydrochloride in 35 ml N,N-dimethylformamide and 1.5 ml N-ethyldiisopropylamine are subsequently added 740 mg 2-(4'-trifluoro-biphenyl-4-yl)-2-hydroxy acetic acid and 1.25 g benzotriazole-1-yloxy-tris(dimethylamino)phosphonium hexafluoro-phosphate. The yellowish solution is stirred over night at 20° C., diluted with ethyl acetate, washed with water and brine and dried over sodium sulfate. The filtrate is evaporated, evaporated and the resulting residue is purified by chromatography (silicagel; hexane-ethyl acetate) leading to the desired 2-(4'-trifluoro-biphenyl-4-yl)-2-hydroxy-N-[2-(3-methoxy-4-prop-2-ynyloxy-phenyl)-ethyl]-acetamide, m.p. 107–109° C.

According to the procedure of Examples E5 and E6 the compounds listed in table E3 are obtained.

TABLE E3

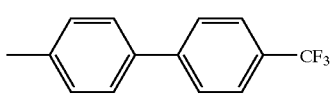

| No. | R₁ | R₄ | R₁₀ | physical data |
|---|---|---|---|---|
| E3.01 | H | HC≡C—CH₂ | 4-Cl—Ph | oil |
| E3.02 | H | HC≡C—CH₂ | 4-Br—Ph | oil |
| E3.03 | H | CH₃ | (4-trifluoromethyl-biphenyl-4-yl) | m.p. 107–109 |

Example E7

N-[2-(3-Methoxy-4-pent-2-ynyloxy-phenyl)-ethyl]-formamide

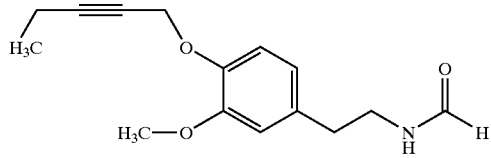

41 ml of a 30% solution of sodium methylate in methanol are added to a solution of 31.5 g (180 mmol) N-[2-(4-hydroxy-3-methoxy-phenyl)-ethyl]-formamide in 880 ml methanol. 48.1 g (184 mmol) toluene-4-sulfonic acid pent-2-ynyl ester are added and the mixture is refluxed for 4 hours. After evaporation the residue is taken up in ethyl acetate and washed with water. After evaporation the residue is submitted to flash-chromatography and crystallisation in ether to give the N-[2-(3-methoxy-4-pent-2-ynyloxy-phenyl)-ethyl]-formamide.

¹H-NMR (300 MHz, CDCl₃): 1.14 (t, 3H, CH₂CH₃), 2.22 (m, 2H, CH₂CH₃), 2.81 (t, 2H, CH₂CH₂), 3.48 and 3.57 (2 q (17:83), 2H, CH₂CH₂), 3.88 (s, 3H, OCH₃), 4.70 (m, 2H, OCH₂), 5.58 (b, 1H, NH), 6.73 (m, 2H, arom.), 6.98 (m, 1H, arom.), 8.14 (s, 1H, CHO).

Example E8
2-(4-Bromo-phenyl)-2-methyloxalyloxy-N-[2-(3-methoxy-4-prop-2-ynyloxy-phenyl)-ethyl]-acetamide

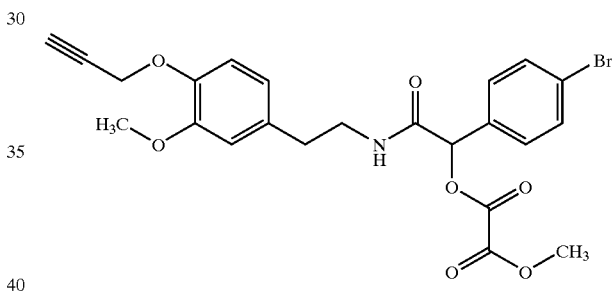

To a solution of 2-(4-bromo-phenyl)-2-hydroxy-N-[2-(3-methoxy-4-prop-2-ynyloxy-phenyl)-ethyl]-acetamide (0.7 g, 1.6 mmol) in 30 ml of methylenchloride is added pyridine (0.3 g, 3.8 mmol). This mixture is cooled to 0° C. and methyl chlorooxoacetate (0.2 g, 1.6 mmol) is added. After 3 hours at room temperature, the solvent is removed in vacuum and the remainder is co-evaporated three times with toluene. The resulting residue is chromatographed on silica gel (ether 60, hexanes 40) to give 2-(4-bromo-phenyl)-2-methyloxalyloxy-N-[2-(3-methoxy-4-prop-2-ynyloxy-phenyl)-ethyl]-acetamide.

¹H-NMR (300 MHz, CDCl₃): 2.31 (t, 1H, C≡CH), 2.59 (m, 2H, CH₂CH₂), 3.35 (m, 2H, CH₂CH₂), 3.62 (s, 3H, OCH₃), 3.70 (s, 3H, OCH₃), 4.54 (s, 2H, OCH₂C≡C), 5.85 (s, 1H, CHC≡O), 6.13 (t, 1H, NH), 6.47 (m, 2H, CH arom.), 6.73 (d, 1H, CH arom.), 7.03 (d, 2H, CH arom.), 7.28 (d, 2H, CH arom.).

According to the procedure of Example E8 the compounds listed in table E4 are obtained.

TABLE E4

| No. | $R_1$ | $R_{10}$ | $R_{16}$ | physical data |
|---|---|---|---|---|
| E4.01 | H | 4-Br—Ph | $CO_2CH_3$ | oil |
| E4.02 | H | 4-Cl—Ph | $CH_3$ | oil |
| E4.03 | H | 4-Cl—Ph | $CH_2CH_3$ | oil |

TABLE E4-continued

| No. | $R_1$ | $R_{10}$ | $R_{16}$ | physical data |
|---|---|---|---|---|
| E4.04 | H | 4-Cl—Ph | $CO_2CH_3$ | m.p. 52 |
| E4.05 | H | 4-Cl—Ph | $CO_2CH_2CH_3$ | m.p. 49 |
| E4.06 | H | 4-Cl—Ph | $CH_2CO_2CH_3$ | oil |
| E4.07 | H | 4-Cl—Ph | Ph | m.p. 53 |

Example E9
2-(1,1-Dimethylethoxycarbonylamino)-N-{2-[3-methoxy-4-(4-chlorophenyl-prop-2-ynyloxy)-phenyl]-ethyl}-3-methylbutyramide

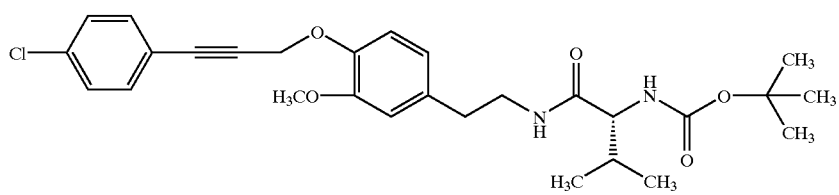

To a mixture of BOC-L-valine (4.7 g), 4-(2-amino-ethyl)-2-methoxy-phenol hydrochloride (4,5 g) and ethyl-diisopropyl-amine (6,5 g) in dimethylformamide (90 ml) is added benzotriazol-1-yloxytris(dimethylamino) phosphonium hexafluorophosphate (9.8 g) in one portion. The mixture is stirred at room temperature for 4 hours. Then water (400 ml) is added. The mixture is extracted with ethyl acetate (2×400 ml) and washed with brine (2×200 ml). The organic layers are collected, dried ($MgSO_4$) and evaporated. 2-(1,1-dimethylethoxycarbonylamino)-N-[2-(4-hydroxy-3-methoxy-phenyl)-ethyl]-3-methylbutyramide is obtained which is purified by flash column chromatography on silica gel (ethyl acetate/hexane 2:3); oil.

To a mixture of 3-(4-chloro-phenyl)-prop-2-yn-1-ol (3.3 g) and toluene-4-sulfonyl chloride (3.7 g) in diethyl ether (100 ml) which is pre-cooled to −15° C. is added powdered potassium hydroxide (2.8 g) in small portions during 10 minutes. The reaction mixture is stirred at 0° C. during 90 minutes. Then water (200 ml) is added and the mixture is extracted with diethyl ether (2×100 ml) and washed with brine (50 ml). The organic layers are collected, dried ($Na_2SO_4$) and evaporated. Toluene-4-sulfonic acid 3-(4-chloro-phenyl)-prop-2-ynyl ester is obtained.

A mixture 2-(1,1-dimethylethoxycarbonylamino)-N-[2-(4-hydroxy-3-methoxy-phenyl)-ethyl]-3-methylbutyramide (4.0 g), toluene-4-sulfonic acid 3-(4-chloro-phenyl)-prop-2-ynyl ester (5.3 g) and 1M sodium methoxide solution in methanol (18 ml) in methanol (100 ml) is heated to reflux for 3 hours. Then the solvent is removed by distillation. Water (300 ml) is added. The mixture is extracted with ethyl acetate (2×200 ml) and washed with brine (100 ml). The organic layers are collected, dried (MgSO$_4$) and evaporated. 2-(1,1-dimethylethoxycarbonylamino)-N-{2-[3-methoxy-4-(4-chlorophenyl-prop-2-ynyloxy)-phenyl]-ethyl}-3-methylbutyramide is obtained which is purified by flash column chromatography on silica gel (ethyl acetate/hexane 1:1) and recrystallisation (ethyl acetate/hexane), m.p. 141–142° C.

According to the procedure of Example E9 the compounds listed in table E5 are obtained.

TABLE E5

| No. | R$_1$ | | R$_{14}$ | R$_{15}$ | physical data |
|---|---|---|---|---|---|
| E5.01 | H | (S) | C$_3$H$_7$-i | C$_3$H$_7$-i | m.p. 165–170 |
| E5.02 | H | (S) | C$_3$H$_7$-i | C$_4$H$_9$-t | m.p. 113–115 |
| E5.03 | C$_2$H$_5$ | (S) | C$_3$H$_7$-i | C$_4$H$_9$-t | m.p.  90–109 |
| E5.04 | 4-Cl-Ph | (S) | C$_3$H$_7$-i | C$_4$H$_9$-t | m.p. 141–142 |
| E5.05 | 4-F-Ph | (S) | C$_3$H$_7$-i | C$_4$H$_9$-t | m.p. 130–133 |
| E5.06 | 4-Cl-Ph | (R) | C$_3$H$_7$-i | C$_3$H$_7$-i | m.p. 172–175 |
| E5.07 | C$_2$H$_5$ | (R) | C$_3$H$_7$-i | C$_3$H$_7$-i | resin |
| E5.08 | H | (R) | C$_3$H$_7$-i | C$_3$H$_7$-i | m.p. 165–166 |
| E5.09 | C$_2$H$_5$ | (S) | C$_3$H$_7$-i | C$_3$H$_7$-i | m.p. 151–152 |

Example E10

N-[2-(3,4-Dihydroxy-phenyl)-ethyl]-formamide

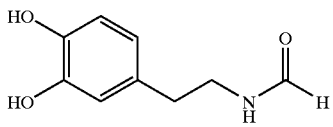

Formic acid (198 ml, 5.26 mol) is added dropwise to 372 ml (3.95 mol) of acetic anhydride at 0° C. This mixture is stirred for 2 hours at 55° C and subsequently cooled again to 0° C. 500 ml Tetrahydrofuran are added at this temperature followed by 50 g (0.26 mol)

3-hydroxytyramine hydrochloride. The resulting white suspension is stirred for 18 hours at 75° C., changing into a yellow solution. The reaction mixture is evaporated and the residue is submitted to flash-chromatography to yield N-[2-(3,4-dihydroxy-phenyl)-ethyl]-formamide.

$^1$H-NMR (300 MHz, CDCl$_3$): 2.72 (t, 2H, CH$_2$CH$_2$), 3.49 (t, 2H, CH$_2$CH$_2$), 6.67–7.20 (m, 3H, CH arom.), 8.04 (s, 1H, CHO).

Example E11

N-[2-(3,4-Bis-prop-2-ynyloxy-phenyl)-ethyl]-formamide

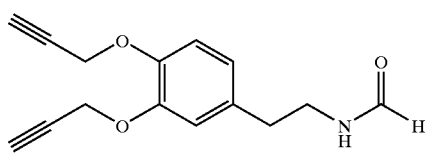

120 ml of a 30% solution of sodium methylate in methanol are added to a solution of 52 g (0.29 mol) N-[2-(3,4-dihydroxy-phenyl)-ethyl]-formamide in 670 ml methanol. 73 g (0.62 mol) propargyl bromide are added and the mixture is refluxed for 4 hours. After evaporation the residue is taken up in ethyl acetate, washed with water and dried over magnesium sulfate. The solvent is removed in vacuum and the remainder is purified by flash-chromatography to give N-[2-(3,4-bis-prop-2-ynyloxy-phenyl)-ethyl]-formamide.

$^1$H-NMR (300 MHz, CDCl$_3$): 2.54 (m, 2H, C≡CH), 2.82 (t, 2H, CH$_2$CH$_2$), 3.57 (t, 2H, CH$_2$CH$_2$), 4.78 (m, 4H, CH$_2$C≡C), 6.81 (d, 1H, CH arom.), 6.90 (s, 1H, CH arom.), 7.04 (d, 1H, CH arom.), 8.19 (s, 1H, CHO).

Example E12

2-(4-Chlorophenyl)-2-hydroxy-N-[2-(3-methoxy-4-prop-2-ynyloxy-phenyl)-ethyl]-2-prop-2-ynyloxy-acetamide

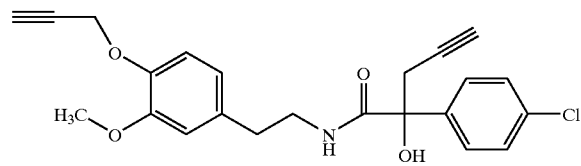

a) 5-(4-Chloro-phenyl)-2,2-dimethyl-5-prop-2-ynyl-(1,3)dioxolan-4-one

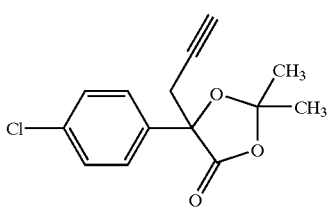

3.3 ml of butyl lithium (1.6 molar in hexane) are added under stirring to a solution of 0.8 ml diisopropylamine in 20 ml tetrahydrofurane at −78° C. under nitrogen. After stirring for 30 minutes at the same temperature, 1.13 g of 5-(4-chloro-phenyl)-2,2-dimethyl-(1,3)-dioxolan-4-one in 5 ml tetrahydrofurane are added and stirring is continued for 1.5 hours. Then the reaction mixture is treated with a solution of 0.57 ml propargyl bromide in 3 ml tetrahydrofurane. Stirring is continued at about 60° C. over the night. Then the reaction is quenched with HCl 1N (pH 6) and ice and water and extracted with diethyl ether. The extracts are dried over sodium sulfate and evaporated. The 5-(4-chloro-phenyl)-2,2-dimethyl-5-prop-2-ynyl-(1,3)dioxolan-4-one remains as a oil which is used directly for the next step.

b) 2-(4-Chlorophenyl)-2-hydroxy-pent-4-ynoic acid

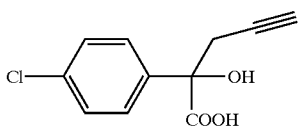

A solution of 530 mg 5-(4-chloro-phenyl)-2,2-dimethyl-5-prop-2-ynyl-(1,3)dioxolan-4-one in 10 ml tetrahydrofurane and 5 ml methanol is treated with 2 ml of 1N NaOH and heated at 60° C. for 1 hour. Then the solution is cooled down, diluted with water and washed with ether. Then the aqueous solution is acidified with 1N HCl and extracted with ethyl acetate. The extracts are dried over sodium sulfate and evaporated to obtain the 2-(4-chlorophenyl)-2-hydroxy-pent-4-ynoic acid of a brownish thick oil which is used for the next step.

c) A suspension of 1.2 g 2-(3-methoxy-4-prop-2-ynyloxy-phenyl)-ethylamine hydrochloride in 50 ml dichloromethane is treated with 1.53 ml N-ethyl-diisopropylamine. To the resulting solution 50 mg of 4-dimethylamino-pyridine and 1.2 g of 2-(4-chlorophenyl-2-hydroxy-pent-4-ynoyl-chloride (freshly prepared from the acid above with oxalyl chloride in dichloromethane) in 15 ml dichloromethane is added dropwise. The reaction mixture is stirred over night at 20° C. and then quenched by pouring onto ice-water. The reaction mixture is extracted with dichloromethane, the extracts are dried over sodium sulfate, filtered and evaporated. HPLC-chromatography of the residue (Lichrophere Si-60/hexane-ethyl acetate) gives the desired 2-(4-chlorophenyl)-2-hydroxy-N-[2-(3-methoxy-4-prop-2-ynyloxy-phenyl)-ethyl]-2-prop-2-ynyloxy-acetamide as a viscous oil.

$^1$H-NMR (CDCl$_3$; ppm): 7.48 (d, 2H); 7.30 (d, 2H); 6.99–6.75 (m, 1H+NH); 6.75–6.56 (m, 2H); 4.72 (m, 2H); 3.83 (s, 1H); 3.80 (s, 3H); 3.48(m, 2H); 3.05 (AB-q, 2H); 2.75 (t, 2H); 2.52 (m, 1H); 2.05 (m, 2H).

The same product 2-(4-chlorophenyl)-2-hydroxy-N-[2-(3-methoxy-4-prop-2-ynyloxy-phenyl)-ethyl]-2-prop-2-ynyloxy-acetamide is obtained when the 5-(4-chloro-phenyl)-2,2-dimethyl-5-prop-2-ynyl-(1,3)dioxolan-4-one is heated with 1.2 equivalents of 2-(3-methoxy-4-but-2-ynyloxy-phenyl)-ethylamine hydrochloride and 1.2 equivalents of DBU 1,8-diazabicyclo(5.4.0)undec-7-ene at 150° C.

Example E13

2-(4-Chlorophenyl)-2-hydroxy-N-[2-(3-methoxy-4-prop-2-ynyloxy-phenyl)-ethyl]propionamide

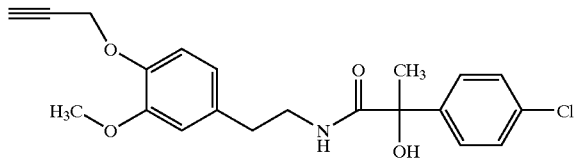

a) 2-(4-Chlorophenyl)-2-hydroxy propionic acid ethyl ester

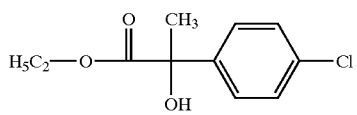

To a stirred solution of 11.5 g ethyl pyruvate in 20 ml diethylether is slowly added under cooling (0° C.), a freshly prepared Grignard solution (from 23.9 g 4-chloro-iodobenzene and 3 g magnesium turnings). Some tetrahydrofurane is added to prevent the formation of viscous suspension. After stirring for 2 hours at room temperature the reaction is quenched by pouring it onto a mixture of ice and 2N sulfuric acid. Extraction of the suspension with diethyl ether followed by washing with brine, drying over sodium sulfate and evaporation leads to a residue which is purified on silicagel (hexane-ethyl acetate) to obtain 2-(4-chlorophenyl)-2-hydroxy propionic acid ethyl ester as yellowish oil.

$^1$H-NMR (CDCl$_3$; ppm): 7.52 (2, 2H); 7.31 (d, 2H); 4.22 (q); 3.82(s, 1H); 1.77 (s, 3H); 1.29 (t, 3H).

b) 2-(4-Chlorophenyl)-2-hydroxy propionic acid

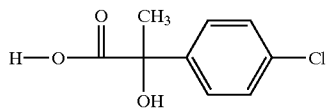

A solution of 5.72 g of the 2-(4-chlorophenyl)-2-hydroxy propionic acid ethyl ester in 170 ml tetrahydrofurane is hydroysed at 0° C. with a solution of 30.5 ml 1N lithium-hydroxide in 19 ml water. When the reaction is complete, the reaction mixture is diluted with water, washed with diethyl ether, acidified with 1N HCl and extracted with ethyl acetate. The extracts are washed with brine, dried over sodium sulfate and evaporated to give 2-(4-chlorophenyl)-2-hydroxy propionic acid.

$^1$H-NMR (CDCl$_3$; ppm): 7.61 (2H, d); 7.32 (2H, d); 4.0–6.5 (broad OH); 10.7 (broad, COOH).

c) To a stirred solution of 906 mg of 2-(3-methoxy-4-but-2-ynyloxy-phenyl)-ethylamine hydrochloride and 2.75 ml N-ethyldiisopropylamine are subsequently added 752 mg 2-(4-chlorophenyl)-2-hydroxy propionic acid and 1.875 g benzotriazole-1-yloxy-tris(dimethylamino)phosphonium hexafluorophosphate. The resulting clear solution is stirred over night, extracted with ethyl acetate. The extracts are washed several times with water, dried over sodium sulfate, filtered and evaporated. The resulting oily residue is purified on silicagel (hexanc ethyl acetate) to obtain the 2-(4-chlorophenyl)-2-hydroxy-N-[2-(3-methoxy-4-prop-2-ynyloxy-phenyl)-ethyl]propionamide.

$^1$H-NMR (CDCl$_3$; ppm): 7.42 (d, 2H); 7.28 (d, 2H); 6.90 (d, 1H) 6.66 (s, 1H); 6.55 (dd, 1H), 6.47 (m, broad, 1H); 4.71 (d, 2H); 3.81 (s, 3H); 3.48 (q, 2H); 3.24 (s, 1H); 2.72 (t, 2H); 2.52 (m, 1H).

Example E14

2-(3',4'-Chloro-biphenyl-4-yl)-2-oxo-acetic acid

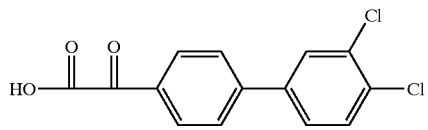

A mixture of 2.2 g 4-bromo-phenyl-oxo acetic acid, 3,4-dichlorophenyl boronic acid and 440 mg palladium 5% on carbon in 2.5 ml 2-propanol and 30 ml water is stirred over night at 65° C. The reaction mixture is then allowed to cool to 40° C. and treated with 30 ml of a mixture of 2-propanol, water and 2N NaOH (70:15:1) and filtered over Hyflo and washed 4 times with 70 ml of the mixture indicated above. The filtrate is acidified with 2N sulfuric acid, the 2-propanol is stripped off and the remaining mixture is allowed to precipitate at 0° C. Filtration gives the 2-(3',4'-chloro-biphenyl-4-yl)-2-oxo-acetic acid as solid, m.p. 168–169.5° C.

Analogously to the above examples the compounds of tables 1 to 48 are obtained.

Ph stands for phenyl

TABLE 1

Compounds represented by the Formula I.1

(I.1)

H—≡—CH$_2$—O—[phenyl with O—CH$_3$]—C(R$_5$)(R$_6$)—C(R$_7$)(R$_8$)—N(H)—C(=O)—C(R$_{11}$)(OH)—R$_{10}$ wherein the combination of the groups R$_5$, R$_6$, R$_7$, R$_8$ and R$_{10}$ corresponds each to one row in table A.

TABLE 2

Compounds represented by the Formula I.2

(I.2)

H$_3$C—≡—CH$_2$—O—[phenyl with O—CH$_3$]—C(R$_5$)(R$_6$)—C(R$_7$)(R$_8$)—N(H)—C(=O)—C(R$_{11}$)(OH)—R$_{10}$ wherein the combination of the groups R$_5$, R$_6$, R$_7$, R$_8$ and R$_{10}$ corresponds each to one row in table A.

TABLE 3

Compounds represented by the Formula I.3

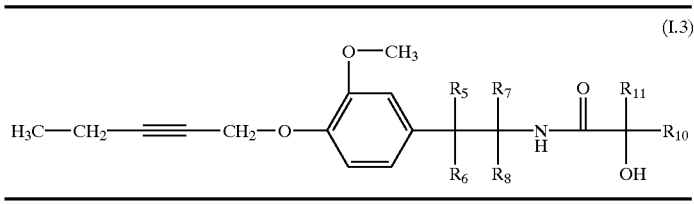
(I.3)

wherein the combination of the groups $R_5$, $R_6$, $R_7$, $R_8$ and $R_{10}$ corresponds each to one row in table A.

TABLE 4

Compounds represented by the Formula I.4

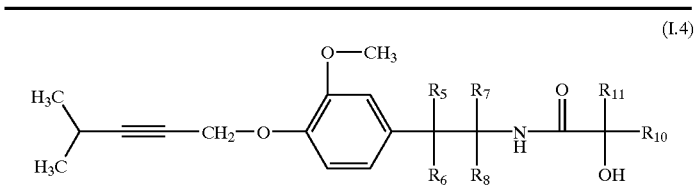
(I.4)

wherein the combination of the groups $R_5$, $R_6$, $R_7$, $R_8$ and $R_{10}$ corresponds each to one row in table A.

TABLE 5

Compounds represented by the Formula I.5

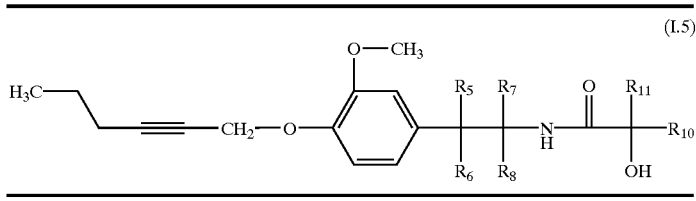
(I.5)

wherein the combination of the groups $R_5$, $R_6$, $R_7$, $R_8$ and $R_{10}$ corresponds to each one row in table A.

TABLE 6

Compounds represented by the Formula I.6

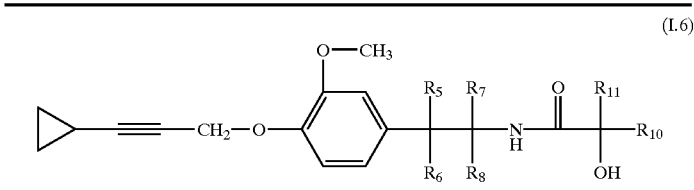
(I.6)

wherein the combination of the groups $R_5$, $R_6$, $R_7$, $R_8$ and $R_{10}$ corresponds each to one row in table A.

TABLE 7
Compounds represented by the Formula I.7
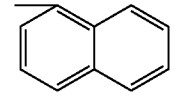
(I.7)
wherein the combination of the groups $R_5$, $R_6$, $R_7$, $R_8$ and $R_{10}$ corresponds each to one row in table A.
TABLE A
| No. | $R_5$ | $R_6$ | $R_7$ | $R_8$ | $R_{11}$ | $R_{10}$ |
|---|---|---|---|---|---|---|
| 01 | H | H | H | H | H | Ph |
| 02 | H | H | H | H | H | 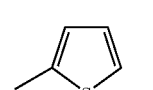 |
| 03 | H | H | H | H | H |  |
| 04 | H | H | H | H | H | 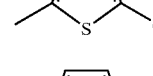 |
| 05 | H | H | H | H | H | 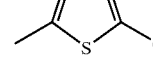 |
| 06 | H | H | H | H | H |  |
| 07 | H | H | H | H | H |  |
| 08 | H | H | H | H | H | 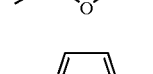 |
| 09 | H | H | H | H | H | 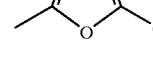 |
| 10 | H | H | H | H | H | 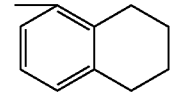 |
| 11 | H | H | H | H | H | |

TABLE A-continued

| No. | $R_5$ | $R_6$ | $R_7$ | $R_8$ | $R_{11}$ | $R_{10}$ |
|---|---|---|---|---|---|---|
| 12 | H | H | H | H | H | 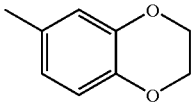 |
| 13 | H | H | H | H | H | 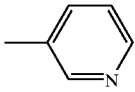 |
| 14 | H | H | H | H | H | 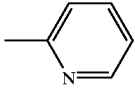 |
| 15 | H | H | H | H | H | 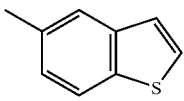 |
| 16 | H | H | H | H | H | 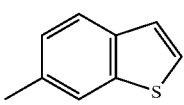 |
| 17 | H | H | H | H | H | 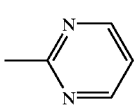 |
| 18 | H | H | H | H | H | 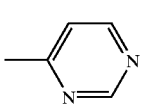 |
| 19 | H | H | H | H | H | 4-F—Ph |
| 20 | H | H | H | H | H | 4-$H_2$C=CH—Ph |
| 21 | H | H | H | H | H | 4-HC≡C—Ph |
| 22 | H | H | H | H | H | 4-$CF_3$—Ph |
| 23 | H | H | H | H | H | 4-$CH_3$O—Ph |
| 24 | H | H | H | H | H | 4-$CF_3$O—Ph |
| 25 | H | H | H | H | H | 4-$CH_3$S—Ph |
| 26 | H | H | H | H | H | 4-$CF_3$S—Ph |
| 27 | H | H | H | H | H | 4-$CH_3SO_2$—Ph |
| 28 | H | H | H | H | H | 4-CN—Ph |
| 29 | H | H | H | H | H | 4-$NO_2$—Ph |
| 30 | H | H | H | H | H | 4-$CH_3$OOC—Ph |
| 31 | H | H | H | H | H | 3-Cl—Ph |
| 32 | H | H | H | H | H | 2-Cl—Ph |
| 33 | H | H | H | H | H | 2,4-$Cl_2$—Ph |
| 34 | H | H | H | H | H | 3,4,5-$Cl_3$—Ph |
| 35 | H | H | H | H | H | 3-Cl-4-F—Ph |
| 36 | H | H | H | H | H | 4-Cl-3-F—Ph |
| 37 | H | H | H | H | H | 4-Cl-3-$CH_3$—Ph |
| 38 | H | H | H | H | H | 4-Cl-3-$CF_3$—Ph |
| 39 | H | H | H | H | H | 3,4-$F_2$—Ph |
| 40 | H | H | H | H | H | 3,4-$Br_2$—Ph |
| 41 | H | H | H | H | H | 3,4-$CH_3$O—Ph |
| 42 | H | H | H | H | H | 3,4-$(CH_3)_2$—Ph |
| 43 | H | H | H | H | H | 3-Cl-4-CN—Ph |
| 44 | H | H | H | H | H | 4-Cl-3-CN—Ph |
| 45 | H | H | H | H | H | 4-Br-3-Cl—Ph |
| 46 | H | H | H | H | H | 3-Br-4-Cl—Ph |
| 47 | H | H | H | H | H | 4-Br-3-$CH_3$—Ph |
| 48 | H | H | H | H | H | 3-Br-4-$CH_3$—Ph |
| 49 | $CH_3$ | H | H | H | H | 4-Cl—Ph |
| 50 | $CH_3$ | $CH_3$ | H | H | H | 4-Cl—Ph |
| 51 | H | H | H | $CH_3$ | H | 4-Cl—Ph |
| 52 | H | H | $CH_3$ | $CH_3$ | H | 4-Cl—Ph |
| 53 | H | H | H | H | $CH_3$ | 4-Cl—Ph |
| 54 | H | H | H | H | $C_2H_5$ | 4-Cl—Ph |
| 55 | H | H | H | $C_2H_5$ | H | 4-Cl—Ph |
| 56 | $CH_3$ | H | H | H | H | 4-Br—Ph |

TABLE A-continued

| No. | R$_5$ | R$_6$ | R$_7$ | R$_8$ | R$_{11}$ | R$_{10}$ |
|---|---|---|---|---|---|---|
| 57 | CH$_3$ | CH$_3$ | H | H | H | 4-Br—Ph |
| 58 | H | H | H | CH$_3$ | H | 4-Br—Ph |
| 59 | H | H | CH$_3$ | CH$_3$ | H | 4-Br—Ph |
| 60 | H | H | H | H | CH$_3$ | 4-Br—Ph |
| 61 | H | H | H | H | C$_2$H$_5$ | 4-Br—Ph |
| 62 | H | H | H | C$_2$H$_5$ | H | 4-Br—Ph |
| 63 | CH$_3$ | H | H | H | H | 4-CH$_3$—Ph |
| 64 | CH$_3$ | CH$_3$ | H | H | H | 4-CH$_3$—Ph |
| 65 | H | H | H | CH$_3$ | H | 4-CH$_3$—Ph |
| 67 | H | H | CH$_3$ | CH$_3$ | H | 4-CH$_3$—Ph |
| 68 | H | H | H | H | CH$_3$ | 4-CH$_3$—Ph |
| 69 | H | H | H | H | C$_2$H$_5$ | 4-CH$_3$—Ph |
| 70 | H | H | H | C$_2$H$_5$ | H | 4-CH$_3$—Ph |
| 71 | CH$_3$ | H | H | H | H | 3,4-Cl$_2$—Ph |
| 72 | CH$_3$ | CH$_3$ | H | H | H | 3,4-Cl$_2$—Ph |
| 73 | H | H | H | CH$_3$ | H | 3,4-Cl$_2$—Ph |
| 74 | H | H | CH$_3$ | CH$_3$ | H | 3,4-Cl$_2$—Ph |
| 75 | H | H | H | H | CH$_3$ | 3,4-Cl$_2$—Ph |
| 76 | H | H | H | H | C$_2$H$_5$ | 3,4-Cl$_2$—Ph |
| 77 | H | H | H | C$_2$H$_5$ | H | 3,4-Cl$_2$—Ph |
| 78 | CH$_3$ | H | H | H | H | 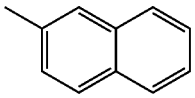 |
| 79 | CH$_3$ | CH$_3$ | H | H | H | 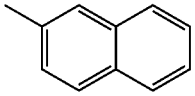 |
| 80 | H | H | H | CH$_3$ | H | 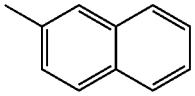 |
| 81 | H | H | CH$_3$ | CH$_3$ | H | 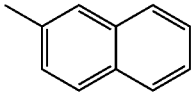 |
| 82 | H | H | H | H | CH$_3$ | 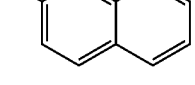 |
| 83 | H | H | H | H | C$_2$H$_5$ | 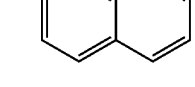 |
| 84 | H | H | H | C$_2$H$_5$ | H | 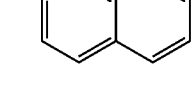 |
| 85 | H | H | H | H | CH$_3$ |  |
| 86 | H | H | H | H | CH$_2$—C≡CH | 4-Cl—Ph |
| 87 | H | H | H | H | CH$_2$—C≡CH | 4-Br—Ph |
| 88 | H | H | H | H | CH$_2$Cl | 4-CH$_3$—Ph |
| 89 | H | H | H | H | CH$_2$—CH=CH$_2$ | 4-CF$_3$—Ph |
| 90 | H | H | H | H | CH$_2$—C≡CHCH$_3$ | 3-Cl—Ph |
| 91 | H | H | H | H | CH$_2$—C≡CHCH$_3$ | 4-CN—Ph |
| 92 | H | H | H | CH$_3$ | CH$_2$—C≡CH | 4-CH$_3$—Ph |
| 93 | H | H | H | H | CH$_2$—CH=CH$_2$ | 3,4-Cl$_2$—Ph |
| 94 | H | H | H | H | CH$_2$—C≡CH | 4-CF$_3$O—Ph |
| 95 | H | H | H | H | CH(CH$_3$)—C≡CH | 4-Cl—Ph |
| 96 | H | H | H | H | CH$_2$Cl | 4-Br—Ph |

TABLE A-continued

| No. | $R_5$ | $R_6$ | $R_7$ | $R_8$ | $R_{11}$ | $R_{10}$ |
|---|---|---|---|---|---|---|
| 97 | H | H | H | $CH_3$ | $CH_2$—CH=$CH_2$ | 4-Cl—Ph |
| 98 | H | H | H | H | $CH_2$—C≡CH | 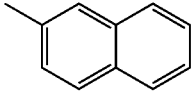 |
| 99 | H | H | H | H | $CH_2$—C≡CH | 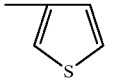 |
| 100 | H | H | H | H | $CH_2Cl$ | 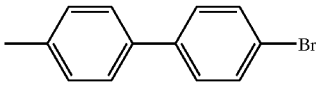 |
| 101 | H | H | H | H | $CH_2$—$CF_3$ | 4-Cl—Ph |
| 102 | H | H | H | H | $CH_3$ | 4-Cl—Ph |
| 103 | H | H | H | H | $CH_2Cl$ | 4-Cl—Ph |

TABLE 8

Compounds represented by the Formula I.8

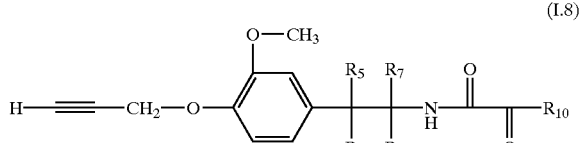

(I.8)

wherein the combination of the groups $R_5$ $R_6$, $R_7$, $R_8$ and $R_{10}$ corresponds each to one row in table B.

TABLE 9

Compounds represented by the Formula I.9

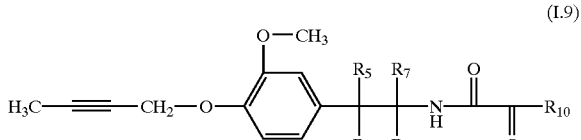

(I.9)

wherein the combination of the groups $R_5$ $R_6$, $R_7$, $R_8$ and $R_{10}$ corresponds each to one row in table B.

TABLE 10

Compounds represented by the Formula I.10

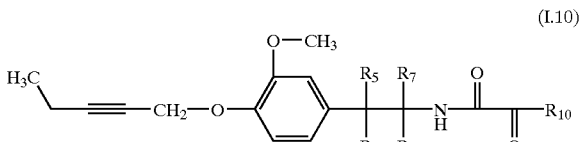

(I.10)

wherein the combination of the groups $R_5$ $R_6$, $R_7$, $R_8$ and $R_{10}$ corresponds each to one row in table B.

TABLE 11

Compounds represented by the Formula I.11

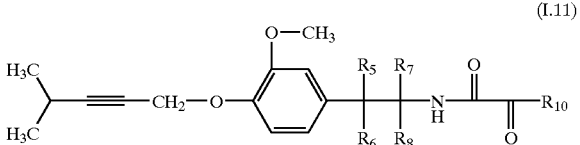

(I.11)

wherein the combination of the groups $R_5$ $R_6$, $R_7$, $R_8$ and $R_{10}$ corresponds each to one row in table B.

TABLE 12

Compounds represented by the Formula I.12

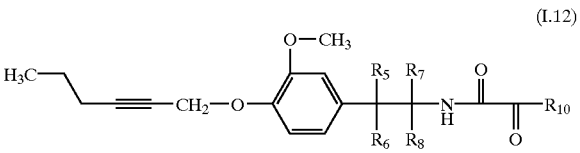

(I.12)

wherein the combination of the groups $R_5$ $R_6$, $R_7$, $R_8$ and $R_{10}$ corresponds each to one row in table B.

TABLE 13

Compounds represented by the Formula I.13

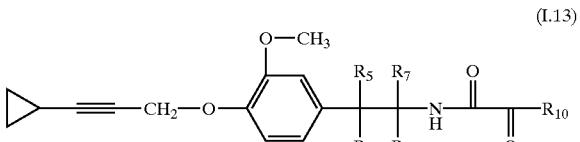

(I.13)

wherein the combination of the groups $R_5$ $R_6$, $R_7$, $R_8$ and $R_{10}$ corresponds each to one row in table B.

TABLE 14

Compounds represented by the Formula I.14

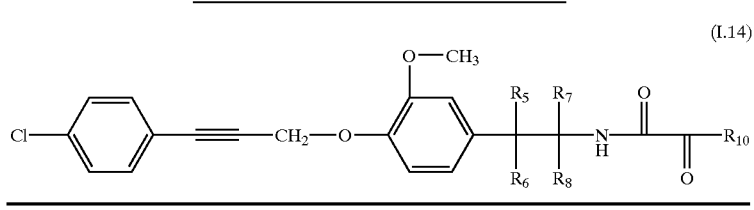
(I.14)

wherein the combination of the groups $R_5$ $R_6$, $R_7$, $R_8$ and $R_{10}$ corresponds each to one row in table B.

TABLE B

| No. | $R_5$ | $R_6$ | $R_7$ | $R_8$ | $R_{10}$ |
|---|---|---|---|---|---|
| 01 | H | H | H | H | Ph |
| 02 | H | H | H | H | naphthyl |
| 03 | H | H | H | H | 2-thienyl |
| 04 | H | H | H | H | 5-chloro-2-thienyl |
| 05 | H | H | H | H | 5-methyl-2-thienyl |
| 06 | H | H | H | H | 3-thienyl |
| 07 | H | H | H | H | 2-furyl |
| 08 | H | H | H | H | 5-methyl-2-furyl |
| 09 | H | H | H | H | 5,6,7,8-tetrahydronaphthyl |
| 10 | H | H | H | H | 5,6,7,8-tetrahydro-2-naphthyl |
| 11 | H | H | H | H | benzo[1,3]dioxol-5-yl |

TABLE B-continued

| No. | R₅ | R₆ | R₇ | R₈ | R₁₀ |
|---|---|---|---|---|---|
| 12 | H | H | H | H | 6-methyl-2,3-dihydro-1,4-benzodioxine |
| 13 | H | H | H | H | 3-methylpyridine |
| 14 | H | H | H | H | 2-methylpyridine |
| 15 | H | H | H | H | 5-methylbenzo[b]thiophene |
| 16 | H | H | H | H | 6-methylbenzo[b]thiophene |
| 17 | H | H | H | H | 2-methylpyrimidine |
| 18 | H | H | H | H | 4-methylpyrimidine |
| 19 | H | H | H | H | 4-F—Ph |
| 20 | H | H | H | H | 4-H₂C=CH—Ph |
| 21 | H | H | H | H | 4-HC≡C—Ph |
| 22 | H | H | H | H | 4-CF₃—Ph |
| 23 | H | H | H | H | 4-CH₃O—Ph |
| 24 | H | H | H | H | 4-CF₃O—Ph |
| 25 | H | H | H | H | 4-CH₃S—Ph |
| 26 | H | H | H | H | 4-CF₃S—Ph |
| 27 | H | H | H | H | 4-CH₃SO₂—Ph |
| 28 | H | H | H | H | 4-CN—Ph |
| 29 | H | H | H | H | 4-NO₂—Ph |
| 30 | H | H | H | H | 4-CH₃OOC—Ph |
| 31 | H | H | H | H | 3-Cl—Ph |
| 32 | H | H | H | H | 2-Cl—Ph |
| 33 | H | H | H | H | 2,4-Cl₂—Ph |
| 34 | H | H | H | H | 3,4,5-Cl₃—Ph |
| 35 | H | H | H | H | 3-Cl-4-F—Ph |
| 36 | H | H | H | H | 4-Cl-3-F—Ph |
| 37 | H | H | H | H | 4-Cl-3-CH₃—Ph |
| 38 | H | H | H | H | 4-Cl-3-CF₃—Ph |
| 39 | H | H | H | H | 3,4-F₂—Ph |
| 40 | H | H | H | H | 3,4-Br₂—Ph |
| 41 | H | H | H | H | 3,4-CH₃O—Ph |
| 42 | H | H | H | H | 3,4-(CH₃)₂—Ph |
| 43 | H | H | H | H | 3-Cl-4-CN—Ph |
| 44 | H | H | H | H | 4-Cl-3-CN—Ph |
| 45 | H | H | H | H | 4-Br-3-Cl—Ph |
| 46 | H | H | H | H | 3-Br-4-Cl—Ph |
| 47 | H | H | H | H | 4-Br-3-CH₃—Ph |
| 48 | H | H | H | H | 3-Br-4-CH₃—Ph |
| 49 | CH₃ | H | H | H | 4-Cl—Ph |
| 50 | CH₃ | CH₃ | H | H | 4-Cl—Ph |
| 51 | H | H | H | CH₃ | 4-Cl—Ph |
| 52 | H | H | CH₃ | CH₃ | 4-Cl—Ph |
| 53 | H | H | H | C₂H₅ | 4-Cl—Ph |
| 54 | CH₃ | H | H | H | 4-Br—Ph |
| 55 | CH₃ | CH₃ | H | H | 4-Br—Ph |
| 56 | H | H | H | CH₃ | 4-Br—Ph |

TABLE B-continued
| No. | R₅ | R₆ | R₇ | R₈ | R₁₀ |
|---|---|---|---|---|---|
| 57 | H | H | CH₃ | CH₃ | 4-Br—Ph |
| 58 | H | H | H | C₂H₅ | 4-Br—Ph |
| 59 | CH₃ | H | H | H | 4-CH₃—Ph |
| 60 | CH₃ | CH₃ | H | H | 4-CH₃—Ph |
| 61 | H | H | H | CH₃ | 4-CH₃—Ph |
| 62 | H | H | CH₃ | CH₃ | 4-CH₃—Ph |
| 63 | H | H | H | C₂H₅ | 4-CH₃—Ph |
| 64 | CH₃ | H | H | H | 3,4-Cl₂—Ph |
| 65 | CH₃ | CH₃ | H | H | 3,4-Cl₂—Ph |
| 67 | H | H | H | CH₃ | 3,4-Cl₂—Ph |
| 68 | H | H | CH₃ | CH₃ | 3,4-Cl₂—Ph |
| 69 | H | H | H | C₂H₅ | 3,4-Cl₂—Ph |
| 70 | CH₃ | H | H | H | 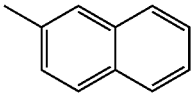 |
| 71 | CH₃ | CH₃ | H | H | 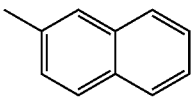 |
| 72 | H | H | H | CH₃ | 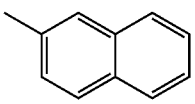 |
| 73 | H | H | CH₃ | CH₃ | 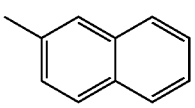 |
| 74 | H | H | H | C₂H₅ | 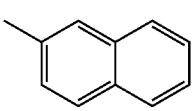 |
| 75 | H | H | H | CH₃ | 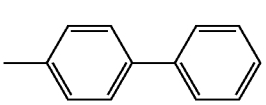 |
| 76 | H | H | H | CH₃ | 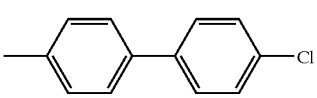 |
| 77 | H | H | H | CH₃ | 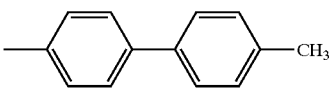 |
| 78 | H | H | H | CH₃ | 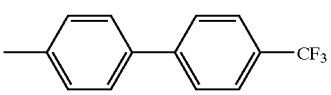 |
| 79 | CH₃ | H | H | H | 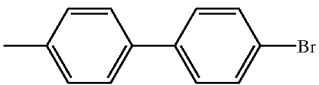 |
| 80 | H | H | H | H | 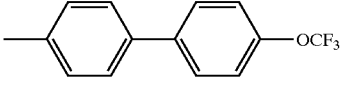 |
| 81 | H | H | CH₃ | H | 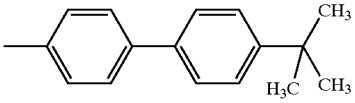 |

TABLE B-continued
| No. | R₅ | R₆ | R₇ | R₈ | R₁₀ |
|-----|----|----|----|----|-----|
| 82 | H | H | H | CH₃ | 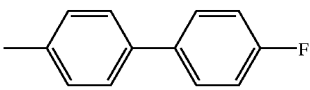 |
| 83 | H | H | H | CH₃ | 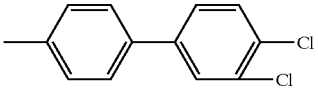 |
| 84 | CH₃ | H | H | H | 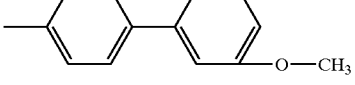 |
| 85 | H | H | H | CH₃ | 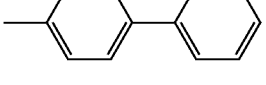 |
| 86 | H | H | CH₃ | CH₃ | 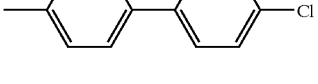 |
| 87 | CH₃ | H | H | CH₃ |  |
| 88 | CH₃ | H | H | H |  |
| 89 | H | H | H | CH₃ |  |
| 90 | H | CH₃ | H | H | 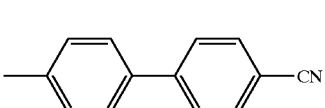 |
| 90 | H | H | H | H | 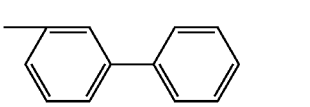 |
| 92 | H | H | H | H | 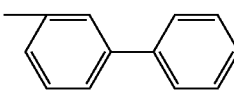 |
| 93 | H | H | H | H | 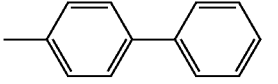 |
| 94 | H | H | H | H | 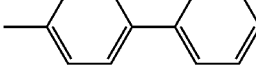 |
| 95 | H | H | H | H |  |

TABLE B-continued

| No. | $R_5$ | $R_6$ | $R_7$ | $R_8$ | $R_{10}$ |
|---|---|---|---|---|---|
| 96 | H | H | H | H | ![biphenyl-Br] |
| 97 | H | H | H | H | ![biphenyl-CH3] |
| 98 | H | H | H | H | ![biphenyl-CF3] |
| 99 | H | H | H | H | ![biphenyl-Br] |

TABLE 15

Compounds represented by the Formula I.15

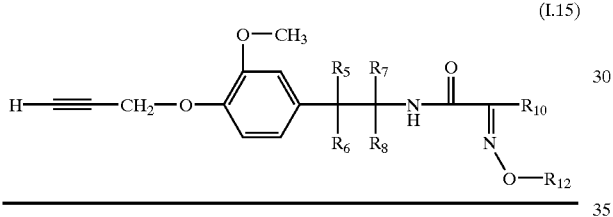

(I.15)

wherein the combination of the groups $R_5$ $R_6$, $R_7$, $R_8$, $R_{10}$ and $R_{12}$ corresponds each to one row in table C.

TABLE 16

Compounds represented by the Formula I.16

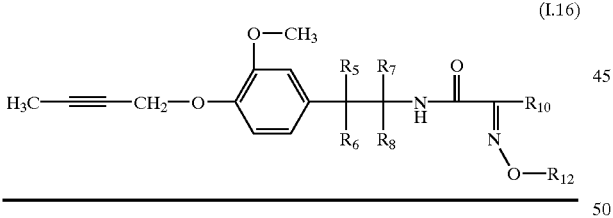

(I.16)

wherein the combination of the groups $R_5$ $R_6$, $R_7$, $R_8$, $R_{10}$ and $R_{12}$ corresponds each to one row in table C.

TABLE 17

Compounds represented by the Formula I.17

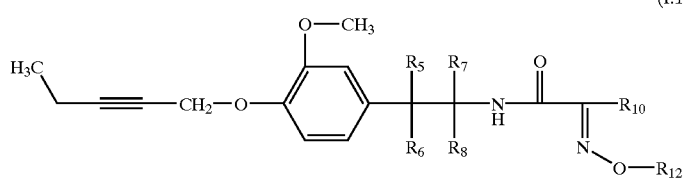

(I.17)

wherein the combination of the groups $R_5$ $R_6$, $R_7$, $R_8$, $R_{10}$ and $R_{12}$ corresponds each to one row in table C.

TABLE 18

Compounds represented by the Formula I.18

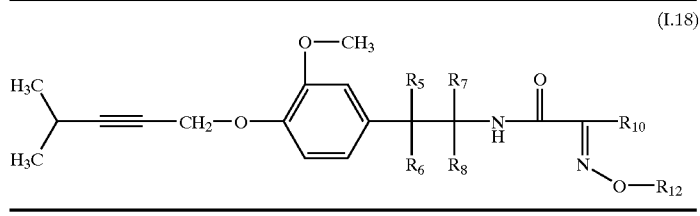

(I.18)

wherein the combination of the groups $R_5$ $R_6$, $R_7$, $R_8$, $R_{10}$ and $R_{12}$ corresponds each to one row in table C.

TABLE 19

Compounds represented by the Formula I.19

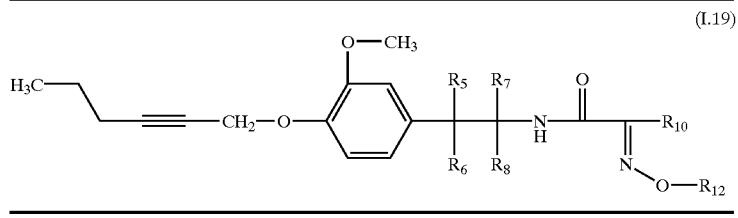

(I.19)

wherein the combination of the groups $R_5$ $R_6$, $R_7$, $R_8$, $R_{10}$ and $R_{12}$ corresponds each to one row in table C.

TABLE 20

Compounds represented by the Formula I.20

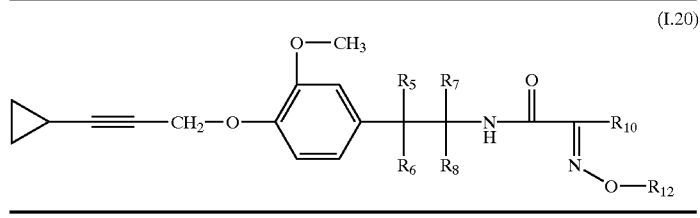

(I.20)

wherein the combination of the groups $R_5$ $R_6$, $R_7$, $R_8$, $R_{10}$ and $R_{12}$ corresponds each to one row in table C.

TABLE 21

Compounds represented by the Formula I.21

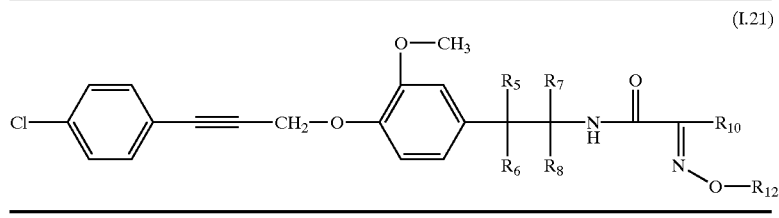

(I.21)

wherein the combination of the groups R₅ R₆, R₇, R₈, R₁₀ and R₁₂ corresponds each to one row table C.
TABLE C
| No. | $R_5$ | $R_6$ | $R_7$ | $R_8$ | $R_{10}$ | $R_{12}$ |
|---|---|---|---|---|---|---|
| 01 | H | H | H | H | Ph | $CH_3$ |
| 02 | H | H | H | H | 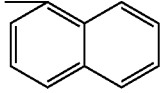 | $CH_3$ |
| 03 | H | H | H | H | 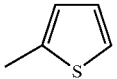 | $CH_3$ |
| 04 | H | H | H | H | 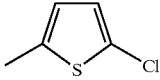 | $CH_3$ |
| 05 | H | H | H | H | 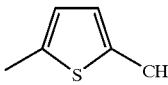 | $CH_3$ |
| 06 | H | H | H | H | 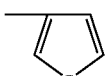 | $CH_3$ |
| 07 | H | H | H | H | 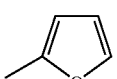 | $CH_3$ |
| 08 | H | H | H | H | 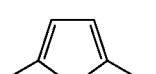 | $CH_3$ |
| 09 | H | H | H | H | 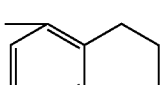 | $CH_3$ |
| 10 | H | H | H | H | 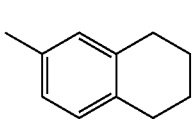 | $CH_3$ |
| 11 | H | H | H | H | 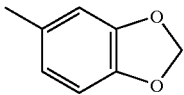 | $CH_3$ |
| 12 | H | H | H | H | 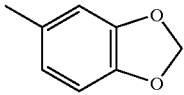 | $CH_3$ |
| 13 | H | H | H | H | 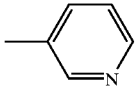 | $CH_3$ |
| 14 | H | H | H | H | 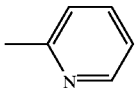 | $CH_3$ |

TABLE C-continued

| No. | R₅ | R₆ | R₇ | R₈ | R₁₀ | R₁₂ |
|---|---|---|---|---|---|---|
| 15 | H | H | H | H | 5-methylbenzo[b]thiophen-2-yl | CH₃ |
| 16 | H | H | H | H | 6-methylbenzo[b]thiophen-2-yl | CH₃ |
| 17 | H | H | H | H | 2-methylpyrimidin-4-yl | CH₃ |
| 18 | H | H | H | H | 4-methylpyrimidin-2-yl | CH₃ |
| 19 | H | H | H | H | 4-F—Ph | CH₃ |
| 20 | H | H | H | H | 4-H₂C=CH—Ph | CH₃ |
| 21 | H | H | H | H | 4-HC≡C—Ph | CH₃ |
| 22 | H | H | H | H | 4-CF₃—Ph | CH₃ |
| 23 | H | H | H | H | 4-CH₃O—Ph | CH₃ |
| 24 | H | H | H | H | 4-CF₃O—Ph | CH₃ |
| 25 | H | H | H | H | 4-CH₃S—Ph | CH₃ |
| 26 | H | H | H | H | 4-CF₃S—Ph | CH₃ |
| 27 | H | H | H | H | 4-CH₃SO₂—Ph | CH₃ |
| 28 | H | H | H | H | 4-CN—Ph | CH₃ |
| 29 | H | H | H | H | 4-NO₂—Ph | CH₃ |
| 30 | H | H | H | H | 4-CH₃OOC—Ph | CH₃ |
| 31 | H | H | H | H | 3-Cl—Ph | CH₃ |
| 32 | H | H | H | H | 2-Cl—Ph | CH₃ |
| 33 | H | H | H | H | 2,4-Cl₂—Ph | CH₃ |
| 34 | H | H | H | H | 3,4,5-Cl₃—Ph | CH₃ |
| 35 | H | H | H | H | 3-Cl-4-F—Ph | CH₃ |
| 36 | H | H | H | H | 4-Cl-3-F—Ph | CH₃ |
| 37 | H | H | H | H | 4-Cl-3-CH₃—Ph | CH₃ |
| 38 | H | H | H | H | 4-Cl-3-CF₃—Ph | CH₃ |
| 39 | H | H | H | H | 3,4-F₂—Ph | CH₃ |
| 40 | H | H | H | H | 3,4-Br₂—Ph | CH₃ |
| 41 | H | H | H | H | 3,4-CH₃O—Ph | CH₃ |
| 42 | H | H | H | H | 3,4-(CH₃)₂—Ph | CH₃ |
| 43 | H | H | H | H | 3-Cl-4-CN—Ph | CH₃ |
| 44 | H | H | H | H | 4-Cl-3-CN—Ph | CH₃ |
| 45 | H | H | H | H | 4-Br-3-Cl—Ph | CH₃ |
| 46 | H | H | H | H | 3-Br-4-Cl—Ph | CH₃ |
| 47 | H | H | H | H | 4-Br-3-CH₃—Ph | CH₃ |
| 48 | H | H | H | H | 3-Br-4-CH₃—Ph | CH₃ |
| 49 | CH₃ | H | H | H | 4-Cl—Ph | CH₃ |
| 50 | CH₃ | CH₃ | H | H | 4-Cl—Ph | CH₃ |
| 51 | H | H | H | CH₃ | 4-Cl—Ph | CH₃ |
| 52 | H | H | CH₃ | CH₃ | 4-Cl—Ph | CH₃ |
| 53 | H | H | H | C₂H₅ | 4-Cl—Ph | CH₃ |
| 54 | H | H | H | H | 4-Cl—Ph | H |
| 55 | H | H | H | H | 4-Cl—Ph | C₂H₅ |
| 56 | H | H | H | H | 4-Cl—Ph | C₃H₇-n |
| 57 | H | H | H | H | 4-Cl—Ph | CH₂—CH=CH₂ |
| 58 | H | H | H | H | 4-Cl—Ph | CH₂—C≡CH |
| 59 | CH₃ | H | H | H | 4-Br—Ph | CH₃ |
| 60 | CH₃ | CH₃ | H | H | 4-Br—Ph | CH₃ |
| 61 | H | H | H | CH₃ | 4-Br—Ph | CH₃ |
| 62 | H | H | CH₃ | CH₃ | 4-Br—Ph | CH₃ |
| 63 | H | H | H | C₂H₅ | 4-Br—Ph | CH₃ |
| 64 | H | H | H | H | 4-Br—Ph | H |
| 65 | H | H | H | H | 4-Br—Ph | C₂H₅ |
| 67 | H | H | H | H | 4-Br—Ph | C₃H₇-n |
| 68 | H | H | H | H | 4-Br—Ph | CH₂—CH=CH₂ |
| 69 | H | H | H | H | 4-Br—Ph | CH₂—C≡CH |
| 70 | CH₃ | H | H | H | 4-CH₃—Ph | CH₃ |
| 71 | CH₃ | CH₃ | H | H | 4-CH₃—Ph | CH₃ |
| 72 | H | H | H | CH₃ | 4-CH₃—Ph | CH₃ |
| 73 | H | H | CH₃ | CH₃ | 4-CH₃—Ph | CH₃ |
| 74 | H | H | H | C₂H₅ | 4-CH₃—Ph | CH₃ |

TABLE C-continued

| No. | R₅ | R₆ | R₇ | R₈ | R₁₀ | R₁₂ |
|---|---|---|---|---|---|---|
| 75 | H | H | H | H | 4-CH₃—Ph | H |
| 76 | H | H | H | H | 4-CH₃—Ph | C₂H₅ |
| 77 | H | H | H | H | 4-CH₃—Ph | C₃H₇-n |
| 78 | H | H | H | H | 4-CH₃—Ph | CH₂—CH=CH₂ |
| 79 | H | H | H | H | 4-CH₃—Ph | CH₂—C≡CH |
| 80 | CH₃ | H | H | H | 3,4-Cl₂—Ph | CH₃ |
| 81 | CH₃ | CH₃ | H | H | 3,4-Cl₂—Ph | CH₃ |
| 82 | H | H | H | CH₃ | 3,4-Cl₂—Ph | CH₃ |
| 83 | H | H | CH₃ | CH₃ | 3,4-Cl₂—Ph | CH₃ |
| 84 | H | H | H | C₂H₅ | 3,4-Cl₂—Ph | CH₃ |
| 85 | H | H | H | H | 3,4-Cl₂—Ph | H |
| 86 | H | H | H | H | 3,4-Cl₂—Ph | C₂H₅ |
| 87 | H | H | H | H | 3,4-Cl₂—Ph | C₃H₇-n |
| 88 | H | H | H | H | 3,4-Cl₂—Ph | CH₂—CH=CH₂ |
| 89 | H | H | H | H | 3,4-Cl₂—Ph | CH₂—C≡CH |
| 90 | CH₃ | H | H | H | 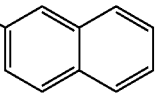 | CH₃ |
| 91 | CH₃ | CH₃ | H | H | 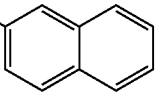 | CH₃ |
| 92 | H | H | H | CH₃ | 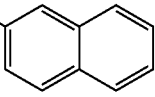 | CH₃ |
| 93 | H | H | CH₃ | CH₃ | 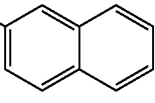 | CH₃ |
| 94 | H | H | H | C₂H₅ | 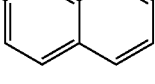 | CH₃ |
| 95 | H | H | H | H | 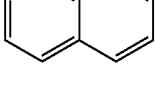 | H |
| 96 | H | H | H | H | 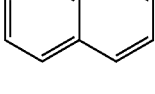 | C₂H₅ |
| 97 | H | H | H | H | 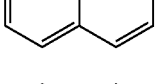 | C₃H₇-n |
| 98 | H | H | H | H | 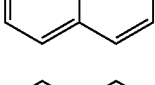 | CH₂—CH=CH₂ |
| 99 | H | H | H | H | 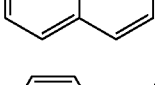 | CH₂—C≡CH |
| 100 | H | H | H | CH₃ | 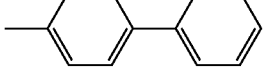 | CH₃ |

TABLE C-continued
| No. | $R_5$ | $R_6$ | $R_7$ | $R_8$ | $R_{10}$ | $R_{12}$ |
|---|---|---|---|---|---|---|
| 101 | H | H | H | $CH_3$ | 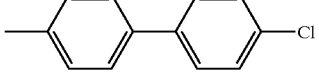 | $CH_3$ |
| 102 | H | H | H | $CH_3$ | 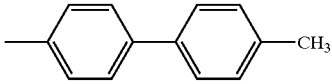 | $CH_3$ |
| 103 | H | H | H | $CH_3$ | 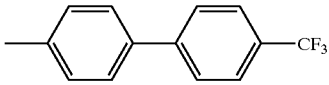 | $CH_3$ |
| 104 | $CH_3$ | H | H | H | 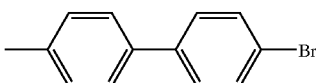 | $CH_3$ |
| 105 | H | H | H | H | 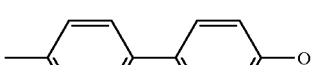 | $C_2H_5$ |
| 106 | H | H | $CH_3$ | H | 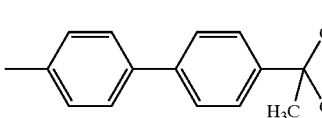 | $CH_2-C\equiv CH$ |
| 107 | H | H | H | $CH_3$ | 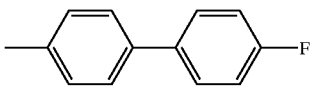 | $CH_3$ |
| 108 | H | H | H | $CH_3$ | 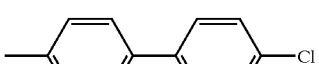 | $CH_2-C\equiv CH$ |
| 109 | $CH_3$ | H | H | H |  | $CH_3$ |
| 110 | H | H | H | $CH_3$ |  | $C_2H_5$ |
| 111 | H | H | $CH_3$ | $CH_3$ |  | $CH_3$ |
| 112 | $CH_3$ | H | H | $CH_3$ |  | $CH_3$ |
| 113 | $CH_3$ | H | H | H |  | $CH_3$ |
| 114 | H | H | H | $CH_3$ |  | $CH_3$ |

TABLE C-continued

| No. | R₅ | R₆ | R₇ | R₈ | R₁₀ | R₁₂ |
|---|---|---|---|---|---|---|
| 115 | H | CH₃ | H | H | —C₆H₄—C₆H₄—Br | CH₃ |
| 116 | H | H | H | H | —C₆H₄—C₆H₄—CN | CH₃ |
| 117 | H | H | H | H | —C₆H₄—C₆H₄ | CH₃ |
| 118 | H | H | H | H | —C₆H₄—C₆H₄—Cl | CH₃ |
| 119 | H | H | H | H | —C₆H₄—C₆H₄ | H |
| 120 | H | H | H | H | —C₆H₄—C₆H₄—Cl | H |
| 121 | H | H | H | H | —C₆H₄—C₆H₄—Br | H |
| 122 | H | H | H | H | —C₆H₄—C₆H₄—CH₃ | H |
| 123 | H | H | H | H | —C₆H₄—C₆H₄—CF₃ | CH₃ |
| 124 | H | H | H | H | —C₆H₄—C₆H₄—Br | C₂H₅ |

TABLE 22

Compounds represented by the Formula I.22

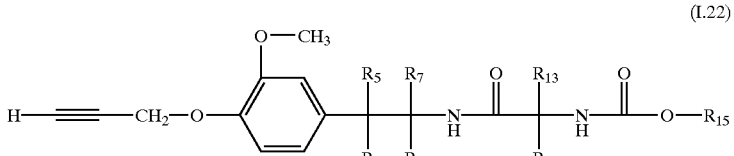

(I.22)

wherein the combination of the groups R₅ R₈, R₇, R₈, R₁₃, R₁₄ and R₁₅ corresponds each to one row in table D.

TABLE 23

Compounds represented by the Formula I.23

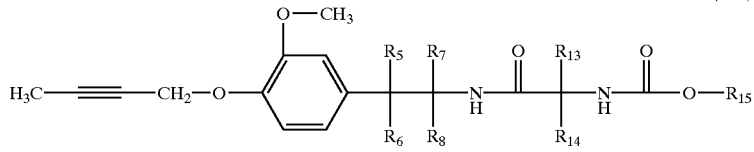
(I.23)

wherein the combination of the groups $R_5$ $R_6$, $R_7$, $R_8$, $R_{13}$, $R_{14}$ and $R_{15}$ corresponds each to one row in table D.

TABLE 24

Compounds represented by the Formula I.24

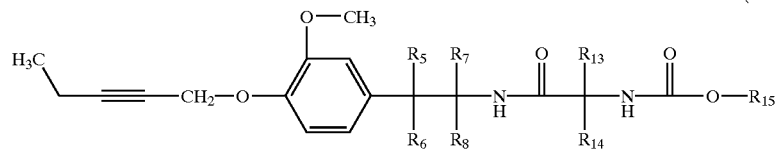
(I.24)

wherein the combination of the groups $R_5$ $R_6$, $R_7$, $R_8$, $R_{13}$, $R_{14}$ and $R_{15}$ corresponds each to one row in table D.

TABLE 25

Compounds represented by the Formula I.25

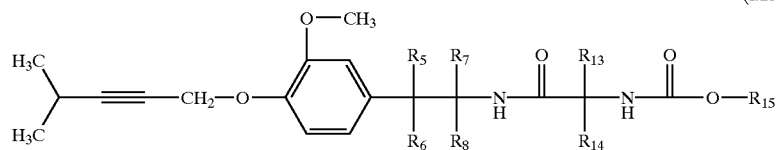
(I.25)

where the combination of the groups $R_5$ $R_6$, $R_7$, $R_8$, $R_{13}$, $R_{14}$ and $R_{15}$ corresponds to each row in table D.

TABLE 26

Compounds represented by the Formula I.26

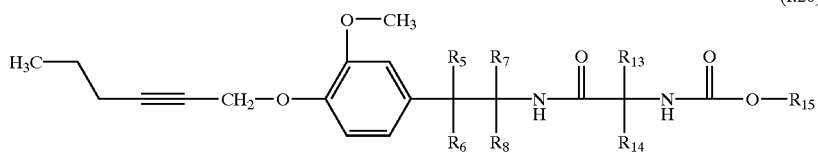
(I.26)

wherein the combination of the groups $R_5$ $R_6$, $R_7$, $R_8$, $R_{13}$, $R_{14}$ and $R_{15}$ corresponds each to one row in table D.

TABLE 27

Compounds represented by the Formula I.27

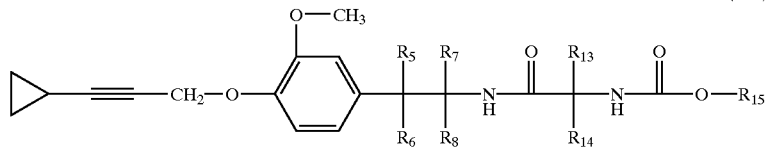

(I.27)

wherein the combination of the groups $R_5$ $R_6$, $R_7$, $R_8$, $R_{13}$, $R_{14}$ and $R_{15}$ corresponds each to one row in table D.

TABLE 28

Compounds represented by the Formula I.28

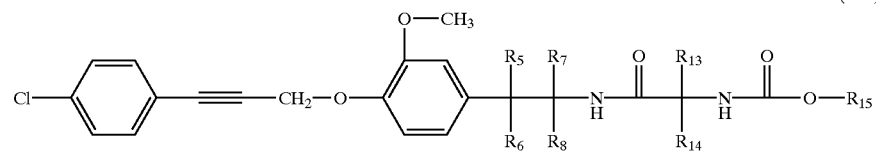

(I.28)

where the combination of the groups $R_5$ $R_6$, $R_7$, $R_8$, $R_{13}$, $R_{14}$ and $R_{15}$ corresponds to each row in table D.

| No | $R_5$ | $R_6$ | $R_7$ | $R_8$ | $R_{13}$ | $R_{14}$ | $R_{15}$ |
|---|---|---|---|---|---|---|---|
| 01 | H | H | H | H | H | $C_4H_9$-s | $C_3H_7$-i |
| 02 | H | H | H | H | H | $C_4H_9$-s | $C_4H_9$-s |
| 03 | H | H | H | H | H | $C_4H_9$-s | $CH_2$-Ph |
| 04 | H | H | H | H | H | $C_4H_9$-s | $CH_2$-(4-Cl-Ph) |
| 05 | H | H | H | H | H | $c_4H_9$-s | $CH_2$-(4-$CH_3$-Ph) |
| 06 | H | H | H | H | H | $C_4H_9$-s | 4-$CH_3$-Ph |
| 07 | H | H | H | H | H | $C_2H_5$ | $C_3H_7$-i |
| 08 | H | H | H | H | H | $C_2H_5$ | $C_4H_9$-s |
| 09 | H | H | H | H | H | $C_2H_5$ | $CH_2$-Ph |
| 10 | H | H | H | H | H | $C_2H_5$ | $CH_2$-(4-Cl-Ph) |
| 11 | H | H | H | H | H | $C_2H_5$ | $CH_2$-(4-$CH_3$-Ph) |
| 12 | H | H | H | H | H | $C_2H_5$ | 4-$CH_3$-Ph |
| 13 | H | H | H | H | H | $C_3H_5$-cycl | $C_3H_7$-i |
| 14 | H | H | H | H | H | $C_3H_5$-cycl | $C_4H_9$-s |
| 15 | H | H | H | H | H | $C_3H_5$-cycl | $CH_2$-Ph |
| 16 | H | H | H | H | H | $C_3H_5$-cycl | $CH_2$-(4-Cl-Ph) |
| 17 | H | H | H | H | H | $C_3H_5$-cycl | $CH_2$-(4-$CH_3$-Ph) |
| 18 | H | H | H | H | H | $C_3H_5$-cycl | 4-$CH_3$-Ph |
| 19 | H | H | H | H | H | $C_6H_{11}$-cycl | $C_3H_7$-i |
| 20 | H | H | H | H | H | $C_6H_{11}$-cycl | $c_4H_9$-s |
| 21 | H | H | H | H | H | $C_6H_{11}$-cycl | $CH_2$-(4-Cl-Ph) |
| 22 | H | H | H | H | H | $C_6H_{11}$-cycl | $CH_2$-(4-$CH_3$-Ph) |
| 23 | H | H | H | H | H | $C_6H_{11}$-cycl | $CH_2$-(4-$CH_3$-Ph) |
| 24 | H | H | H | H | H | $C_6H_{11}$-cycl | 4-$CH_3$Ph |
| 25 | H | H | H | H | H | $C_3H_7$-n | $C_3H_7$-i |
| 26 | H | H | H | H | H | $C_3H_7$-n | $C_4H_9$-s |
| 27 | H | H | H | H | H | $C_3H_7$-n | $CH_2$-Ph |
| 28 | H | H | H | H | H | $C_3H_7$-n | $CH_2$-(4-Cl-Ph) |
| 29 | H | H | H | H | H | $C_3H_7$-n | $CH_2$-(4-$CH_3$-Ph) |
| 30 | H | H | H | H | H | $C_3H_7$-n | 4-$CH_3$-Ph |
| 31 | H | H | H | H | H | $C_3H_7$-i | $C_3H_7$-i |
| 32 | H | H | H | H | H | $C_3H_7$-i | $C_4H_9$-s |
| 33 | H | H | H | H | H | $C_3H_7$-i | $CH_2$-Ph |
| 34 | H | H | H | H | H | $C_3H_7$-i | $CH_2$-(4-Cl-Ph) |
| 35 | H | H | H | H | H | $C_3H_7$-i | $CH_2$(4-$CH_3$-Ph) |
| 36 | H | H | H | H | H | $C_3H_7$-i | 4-$CH_3$-Ph |
| 37 | H | H | H | H | H | $C_3H_7$-i | $C_2H_5$ |
| 38 | H | H | H | H | H | $C_3H_7$-i | $C_3H_7$-n |
| 39 | H | H | H | H | H | $C_3H_7$-i | $C_4H_9$-n |
| 40 | H | H | H | H | H | $C_3H_7$-i | $C_4H_9$-i |
| 41 | H | H | H | H | H | $C_3H_7$-i | $CH_2$-CH=$CH_2$ |
| 42 | H | H | H | H | H | $C_3H_7$-i | $CH_2$-C($CH_3$)=$CH_2$ |
| 43 | H | H | H | H | H | $C_3H_7$-i | $CH_2$C≡CH |
| 44 | H | H | H | H | H | $C_3H_7$-i | 4-Cl-Ph |
| 45 | H | H | H | H | H | $C_3H_7$-i | $CH_2$-(4-Cl-Ph) |
| 46 | H | H | H | H | H | $C_3H_7$-i | 3-$CF_3$-Ph |
| 47 | H | H | H | H | H | $C_3H_7$-i | 4-$CH_3O$-Ph |
| 48 | H | H | H | H | H | $C_3H_7$-i | $CH_2$-(4-$CH_3O$-Ph) |
| 49 | $CH_3$ | H | H | H | H | $C_3H_7$-i | $C_3H_7$-i |
| 50 | $CH_3$ | $CH_3$ | H | H | H | $C_3H_7$-i | $C_3H_7$-i |
| 51 | H | H | $CH_3$ | H | H | $C_3H_7$-i | $C_3H_7$-i |
| 52 | H | H | $CH_3$ | $CH_3$ | H | $C_3H_7$-i | $C_3H_7$-i |
| 53 | H | H | H | $C_2H_5$ | H | $C_3H_7$-i | $C_3H_7$-i |
| 54 | $CH_3$ | H | H | H | H | $C_3H_7$-i | $C_4H_9$-s |
| 55 | $CH_3$ | $CH_3$ | H | H | H | $C_3H_7$-i | $C_4H_9$-s |
| 56 | H | H | H | $CH_3$ | H | $C_3H_7$-i | $C_4H_9$-s |
| 57 | H | H | $CH_3$ | $CH_3$ | H | $C_3H_7$-i | $C_4H_9$-s |
| 58 | H | H | H | $C_2H_5$ | H | $C_3H_7$-i | $C_4H_9$-s |
| 59 | $CH_3$ | H | H | H | H | $C_3H_7$-i | $CH_2$Ph |
| 60 | $CH_3$ | $CH_3$ | H | H | H | $C_3H_7$-i | $CH_2$Ph |
| 61 | H | H | H | $CH_3$ | H | $C_3H_7$-i | $CH_2$Ph |
| 62 | H | H | $CH_3$ | $CH_3$ | H | $C_3H_7$-i | $CH_2$Ph |
| 63 | H | H | H | $C_2H_5$ | H | $C_3H_7$-i | $CH_2$Ph |
| 64 | $CH_3$ | H | H | H | H | $C_3H_7$-i | $CH_2$-(4-Cl-Ph) |
| 65 | $CH_3$ | $CH_3$ | H | H | H | $C_3H_7$-i | $CH_2$-(4-Cl-Ph) |
| 67 | H | H | H | $CH_3$ | H | $C_3H_7$-i | $CH_2$-(4-Cl-Ph) |
| 68 | H | H | $CH_3$ | $CH_3$ | H | $C_3H_7$-i | $CH_2$-(4-Cl-Ph) |
| 69 | H | H | H | $C_2H_5$ | H | $C_3H_7$-i | $CH_2$-(4-Cl-Ph) |
| 70 | $CH_3$ | H | H | H | H | $C_3H_7$-i | $CH_2$(4-$CH_3$-Ph) |
| 71 | $CH_3$ | $CH_3$ | H | H | H | $C_3H_7$-i | $CH_2$(4-$CH_3$-Ph) |
| 72 | H | H | H | $CH_3$ | H | $C_3H_7$-i | $CH_2$(4-$CH_3$-Ph) |
| 73 | H | H | $CH_3$ | $CH_3$ | H | $C_3H_7$-i | $CH_2$(4-$CH_3$-Ph) |
| 74 | H | H | H | $C_2H_5$ | H | $C_3H_7$-i | $CH_2$(4-$CH_3$-Ph) |

TABLE 29

Compounds represented by the Formula I.29

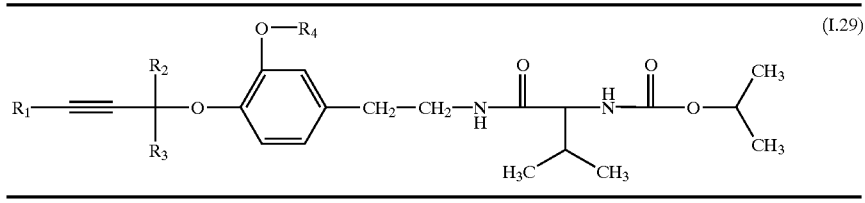
(I.29)

wherein the combination of the groups $R_1$, $R_2$, $R_3$ and $R_4$ corresponds each to one row in table F.

TABLE 30

Compounds represented by the Formula I.30

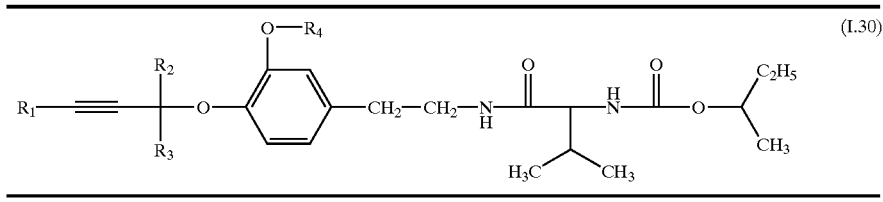
(I.30)

wherein the combination of the groups $R_1$, $R_2$, $R_3$ and $R_4$ corresponds each to one row in table F.

TABLE 31

Compounds represented by the Formula I.31

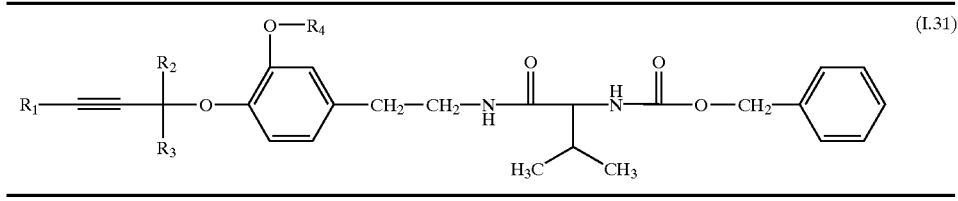
(I.31)

wherein the combination of the groups $R_1$, $R_2$, $R_3$ and $R_4$ corresponds each to one row in table F.

TABLE 32

Compounds represented by the Formula I.32

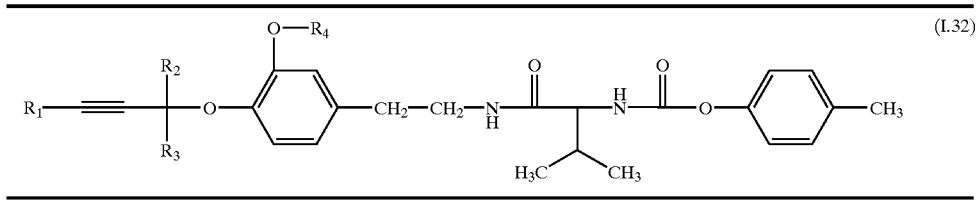
(I.32)

wherein the combination of the groups $R_1$, $R_2$, $R_3$ and $R_4$ corresponds each to one row in table F.

TABLE 33

Compounds represented by the Formula I.33

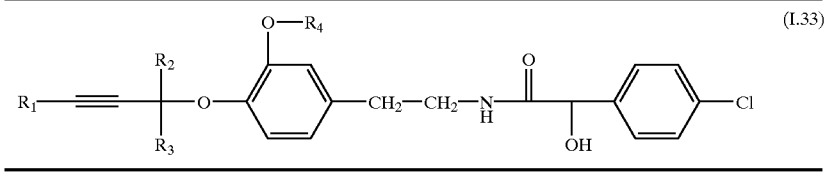
(I.33)

wherein the combination of the groups $R_1$, $R_2$, $R_3$ and $R_4$ corresponds each to one row in table F.

TABLE 34

Compounds represented by the Formula I.34

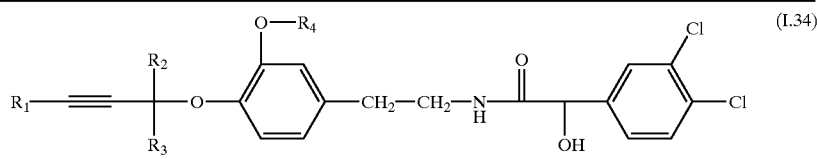
(I.34)

wherein the combination of the groups $R_1$, $R_2$, $R_3$ and $R_4$ corresponds each to one row in table F.

TABLE 35

Compounds represented by the Formula I.35

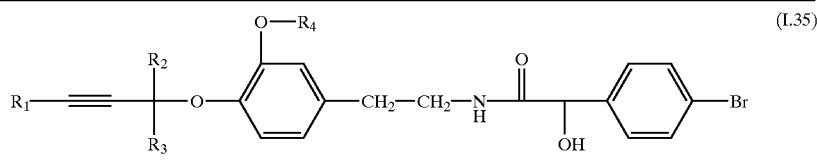
(I.35)

wherein the combination of the groups $R_1$, $R_2$, $R_3$ and $R_4$ corresponds each to one row in table F.

TABLE 36

Compounds represented by the Formula I.36

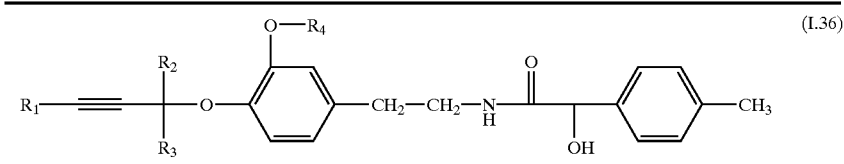
(I.36)

wherein the combination of the groups $R_1$, $R_2$, $R_3$ and $R_4$ corresponds each to one row in table F.

TABLE 37

Compounds represented by the Formula I.37

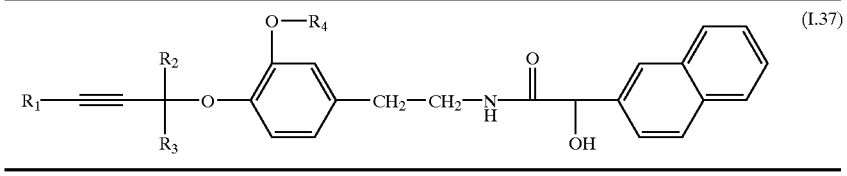
(I.37)

wherein the combination of the groups $R_1$, $R_2$, $R_3$ and $R_4$ corresponds each to one row in table F.

TABLE 38

Compounds represented by the Formula I.38

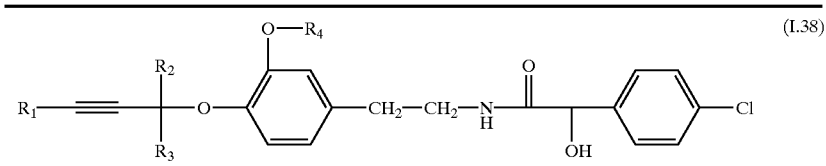
(I.38)

wherein the combination of the groups $R_1$, $R_2$, $R_3$ and $R_4$ corresponds each to one row in table F.

TABLE 39

Compounds represented by the Formula I.39

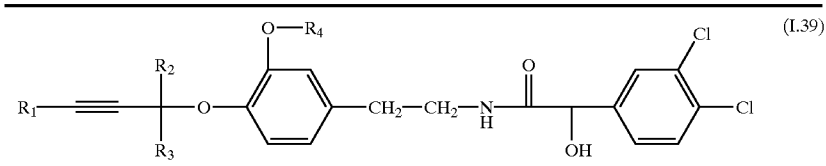
(I.39)

wherein the combination of the groups $R_1$, $R_2$, $R_3$ and $R_4$ corresponds each to one row in table F.

TABLE 40

Compounds represented by the Formula I.40

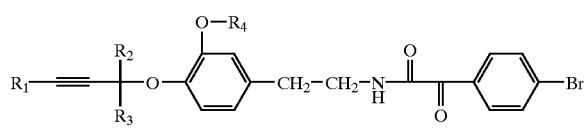
(I.40)

wherein the combination of the groups $R_1$, $R_2$, $R_3$ and $R_4$ corresponds each to one row in table F.

TABLE 41

Compounds represented by the Formula I.41

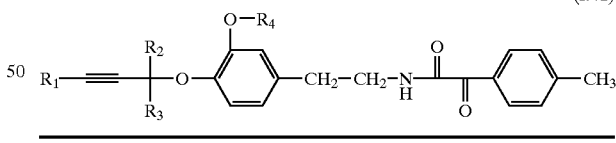
(I.41)

wherein the combination of the groups $R_1$, $R_2$, $R_3$ and $R_4$ corresponds each to one row in table F.

TABLE 42

Compounds represented by the Formula I.42

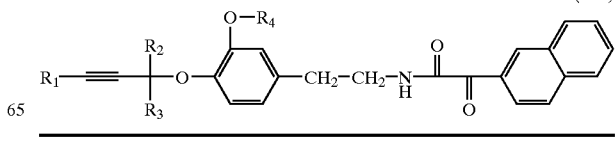
(I.42)

wherein the combination of the groups $R_1$, $R_2$, $R_3$ and $R_4$ corresponds each to one row in table F.

TABLE 43

Compounds represented by the Formula I.43

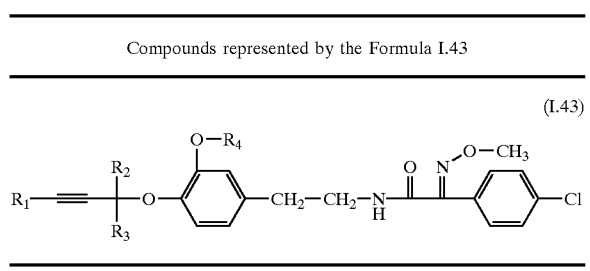
(I.43)

wherein the combination of the groups $R_1$, $R_2$, $R_3$ and $R_4$ corresponds each to one row in table F.

TABLE 44

Compounds represented by the Formula I.44

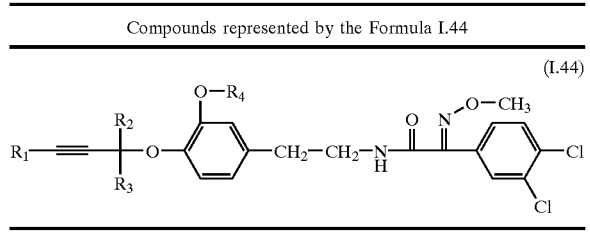
(I.44)

wherein the combination of the groups $R_1$, $R_2$, $R_3$ and $R_4$ corresponds each to one row in table F.

TABLE 45

Compounds represented by the Formula I.45

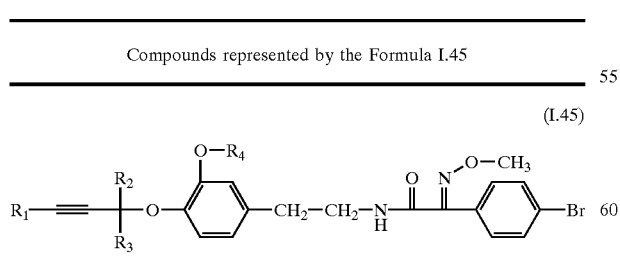
(I.45)

wherein the combination of the groups $R_1$, $R_2$, $R_3$ and $R_4$ corresponds each to one row in table F.

TABLE 46

Compounds represented by the Formula I.46

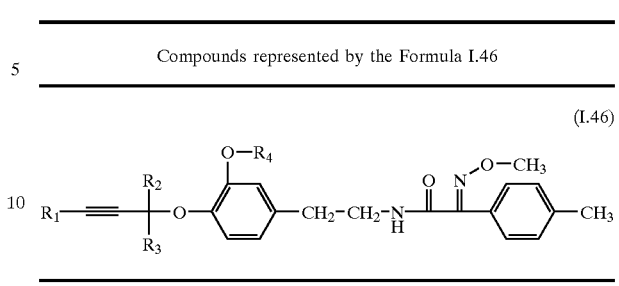
(I.46)

wherein the combination of the groups $R_1$, $R_2$, $R_3$ and $R_4$ corresponds each to one row in table F.

TABLE 47

Compounds represented by the Formula I.47

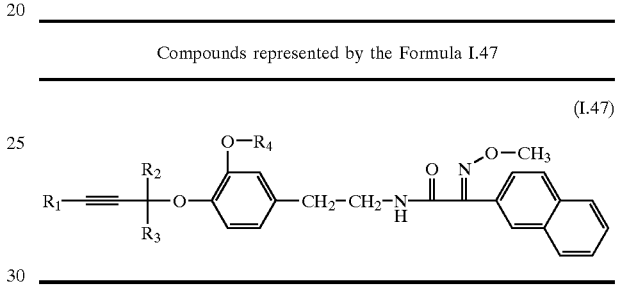
(I.47)

wherein the combination of the groups $R_1$, $R_2$, $R_3$ and $R_4$ corresponds each to one row in table F.

TABLE 48

Compounds represented by the Formula I.48

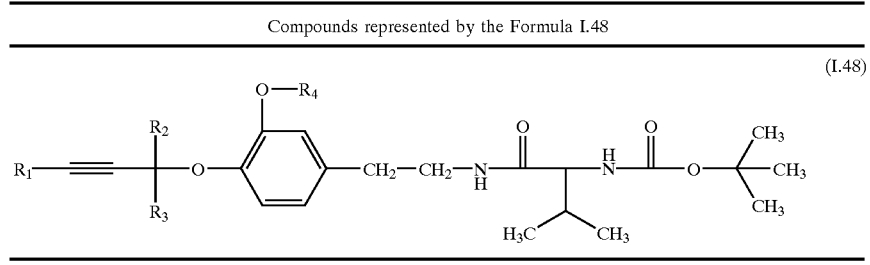
(I.48)

wherein the combination of the groups $R_1$, $R_2$, $R_3$ and $R_4$ corresponds each to one row in table F.

TABLE F

| No. | $R_1$ | $R_2$ | $R_3$ | $R_4$ |
|---|---|---|---|---|
| 01 | H | H | H | $CH_3$ |
| 02 | $CH_3$ | H | H | $CH_3$ |
| 03 | $C_2H_5$ | H | H | $CH_3$ |
| 04 | $C_3H_7$-n | H | H | $CH_3$ |
| 05 | $C_3H_7$-i | H | H | $CH_3$ |
| 06 | $C_3H_5$-cycl | H | H | $CH_3$ |
| 07 | $C_4H_9$-n | H | H | $CH_3$ |
| 08 | $C_4H_9$-i | H | H | $CH_3$ |
| 09 | $C_4H_9$-s | H | H | $CH_3$ |
| 10 | $C_4H_9$-t | H | H | $CH_3$ |
| 11 | $C_5H_{11}$-n | H | H | $CH_3$ |
| 12 | $C_5H_9$-cycl | H | H | $CH_3$ |

TABLE F-continued

| No. | $R_1$ | $R_2$ | $R_3$ | $R_4$ |
|---|---|---|---|---|
| 13 | $C_6H_{11}$-cycl | H | H | $CH_3$ |
| 14 | Ph | H | H | $CH_3$ |
| 15 | 4-F—Ph | H | H | $CH_3$ |
| 16 | 4-Cl—Ph | H | H | $CH_3$ |
| 17 | 4-Br—Ph | H | H | $CH_3$ |
| 18 | 4-$CH_3$—Ph | H | H | $CH_3$ |
| 19 | 4-$CH_3$O—Ph | H | H | $CH_3$ |
| 20 | 4-$NO_2$—Ph | H | H | $CH_3$ |
| 21 | 4-$CF_3$—Ph | H | H | $CH_3$ |
| 22 | 4-$CH_3$OOC—Ph | H | H | $CH_3$ |
| 23 | 4-$CH_3$CO—Ph | H | H | $CH_3$ |
| 24 | 3-F—Ph | H | H | $CH_3$ |
| 25 | 3-Cl—Ph | H | H | $CH_3$ |
| 26 | 3-$CH_3$—Ph | H | H | $CH_3$ |
| 27 | 3-$CF_3$—Ph | H | H | $CH_3$ |
| 28 | 2-Cl—Ph | H | H | $CH_3$ |
| 29 | 2-Br—Ph | H | H | $CH_3$ |
| 30 | 2,4-$Cl_2$—Ph | H | H | $CH_3$ |
| 31 | 4-Cl-2-F—Ph | H | H | $CH_3$ |
| 32 | 3,4-$F_2$—Ph | H | H | $CH_3$ |
| 33 | 3,4-$Cl_2$—Ph | H | H | $CH_3$ |
| 34 | 3,4-$(CH_3)_2$—Ph | H | H | $CH_3$ |
| 35 | 3-Cl-4-$CH_3$—Ph | H | H | $CH_3$ |
| 36 | 4-Cl-3-$CH_3$—Ph | H | H | $CH_3$ |
| 37 | 3-Cl-4-F—Ph | H | H | $CH_3$ |
| 38 | 4-Cl-3-F—Ph | H | H | $CH_3$ |
| 39 | 2,4,5-$Cl_3$—Ph | H | H | $CH_3$ |
| 40 | naphthyl | H | H | $CH_3$ |
| 41 | methyl-naphthyl | H | H | $CH_3$ |
| 42 | H | $CH_3$ | H | $CH_3$ |
| 43 | H | $CH_3$ | $CH_3$ | $CH_3$ |
| 44 | H | H | H | $C_2H_5$ |
| 45 | H | H | H | $CH_2$—CH=$CH_2$ |
| 46 | H | H | H | $CH_2$—C≡CH |

Formulations may be prepared analogously to those described in, for example, WO 95/30651.

BIOLOGICAL EXAMPLES

D-1: Action Against *Plasmopara viticola* on Vines a) Residual-Protective Action Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and +20° C.

b) Residual-curative Action

Vine seedlings are infected at the 4- to 5-leaf stage with a sporangia suspension of the fungus. After incubation for 24 hours in a humidity chamber at 95–100% relative humidity and +20° C., the infected plants are dried and sprayed with a spray mixture (0.02% active ingredient) prepared from a wettable powder formulation of the test compound. After the spray coating has dried, the treated plants are placed in the humidity chamber again.

Fungus infestation is evaluated 6 days after infection.

Compounds of Tables 1 to 47 exhibit a good fungicidal action against *Plasmopara viticola* on vines. Compounds E1.01, E1.02, E1.05, E1.06, E1.08, E1.13, E1.21. E1.30. E1.40, E1.42, E1.42, E1.46, E1.48, E1.49, E1.50, E1.53, E1.55, E1.56, E1.57, Ea1.01, Ea1.02, E2.01, E2.02, E2.06, E2.07, E2.08, E2.14, E2.19, E2.26, E3.01, E3.02, E3.03, E3.05, E4.01 and 1.86 completely inhibit fungal infestation in this test.

D-2: Action Against Phytophthora on Tomato Plants a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and +20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and +20° C.

Compounds of Tables 1 to 47 exhibit a long-lasting effect against fungus infestation.

Compounds E1.01, E1.02, E1.05, E1.06, E1.08, E1.13, E1.21. E1.30. E1.40, E1.42, E1.42, E1.46, E1.48, E1.49, E1.50, E1.53, E1.55, E1.56, E1.57, Ea1.01, Ea1.02, E2.01, E2.02, E2.06, E2.07, E2.08, E2.14, E2.19, E2.26, E3.01, E3.02, E3.03, E3.05, E4.01 and 1.86 completely inhibit fungal infestation in this test.

ID-3: Action Against Phytophthora on Potato Plants a) Residual-protective Action 2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and +20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and +20° C. Fungal infestation is effectively controlled with compounds of Tables 1 to 47.

Compounds E1.01, E1.02, E1.06, E1.08, E1.13, E1.30, E1.40, E1.41, E1.42, E1.48, E1.49, E1.53, E1.55, E1.56, E2.06, E2.07, E2.19, E3.01 and E3.02 completely inhibit fungal infestation in this test.

What is claimed is:

1. Propargylether derivatives of formula I

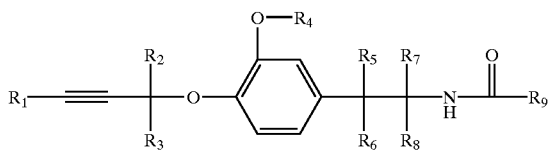

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl and $R_9$ is a group

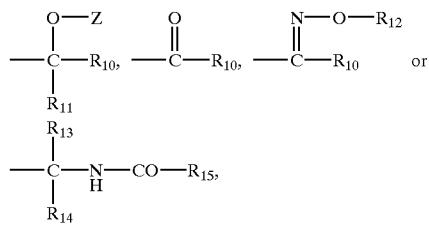

$R_{10}$ is optionally substituted aryl or optionally substituted heteroaryl, $R_{11}$ is hydrogen or optionally substituted alkyl, alkenyl or alkynyl, Z is hydrogen —CO—$R_{16}$, —COO$R_{16}$, —CO—COO$R_{16}$ or —CONR$_{16}$R$_{17}$, $R_{12}$ is hydrogen, or optionally substituted alkyl, alkenyl or alkynyl, $R_{13}$ is hydrogen or alkyl, $R_{14}$ is hydrogen, alkyl, cycloalkyl or cycloalkyl-alkyl, $R_{15}$ is alkyl, alkenyl, alkynyl, optionally substituted aryl or optionally substituted aryl-alkyl, and $R_{16}$ and $R_{17}$ are independently of each other hydrogen, optionally substituted alkyl, optionally substituted cycloalkyl, optionally substituted aryl or optionally substituted heteroaryl.

2. A compound according to claim 1 wherein $R_{11}$ is hydrogen or alkyl,

Z is hydrogen or —CO—$R_{16}$, $R_{12}$ is hydrogen, alkyl, alkenyl or alkynyl, and $R_{16}$ is hydrogen or alkyl.

3. A compound of formula I according to claim 1 selected from the group consisting of 2-(3,4-dichloro-phenyl)-2-hydroxy-N-[2-(3-methoxy-4-prop-2-ynyloxy-phenyl)-ethyl]-acetamide, 2-(3,4-dichloro-phenyl)-2-hydroxy-N-[2-(3-methoxy-4-pent-2-ynyloxy-phenyl)-ethyl]-acetamide, 2-(4-fluorophenyl)-2-hydroxy-N-[2-(3-methoxy-4-prop-2-ynyloxy-phenyl)-ethyl]-acetamide, 2-(4chloro-phenyl)-2-hydroxy-N-[2-(3-methoxy-4-prop-2-ynyloxy-phenyl)-ethyl]-acetamide, 2-(4-bromo-phenyl)-2-hydroxy-N-[2-(3-methoxy-4prop-2-ynyloxy-phenyl)-ethyl]-acetamide, 2-(4-methoxy-phenyl)-2-hydroxy-N-[2-(3-methoxy-4-prop-2-ynyloxy-phenyl)-ethyl]-acetamide, 2-(4-methyl-phenyl)-2-hydroxy-N-[2-(3-methoxy-4-prop-2-ynyloxy-phenyl)-ethyl]-acetamide 2-(2-naphthyl)-2-hydroxy-N-[2-(3-methoxy-4-prop-2-ynyloxy-phenyl)-ethyl]-acetamide, 2-(3,4-dichloro-phenyl)-N-[2-(3-methoxy-4-prop-2-ynyloxy-phenyl)-ethyl]-2-oxo-acetamide, 2-(3,4-dichloro-phenyl)-N-[2-(3-methoxy-4-pent-2-ynyloxy-phenyl)-ethyl]-2-oxo-acetamide, 2-(4-chloro-phenyl)-N-[2-(3-methoxy-4-prop-2-ynyloxy-phenyl)-ethyl]-2-oxo-acetamide, 2-(4-bromo-phenyl)-N-[2-(3-methoxy-4-prop-2-ynyloxy-phenyl)-ethyl]-2-oxo-acetamide, 2-(4-methyl-phenyl)-N-[2-(3-methoxy-4-prop-2-ynyloxy-phenyl)-ethyl]-2-oxo-acetamide, 2-(3,4-dimethoxy-phenyl)-N-[2-(3-methoxy-4-prop-2-ynyloxy-phenyl)-ethyl]-2-oxo-acetamide, 2-(1-methylethoxycarbonylamino)-N-[2-(3-methoxy-4-prop-2-ynyloxy-phenyl)-ethyl]-3-methylbutyramide, 2-(1,1-dimethylethoxycarbonylamino)-N-[2-(3-methoxy-4-prop-2-ynyloxy-phenyl)-ethyl]-3-methylbutyramide, 2-(1,1-dimethylethoxycarbonylamino)-N-{2-[3-methoxy-4-(pent-2-ynyloxy)-phenyl]-ethyl}-3-methylbutyramide, 2-(1,1-dimethylethoxycarbonylamino)-N-{2-[3-methoxy-4-(4-fluorophenylprop-2-ynyloxy)-phenyl]-ethyl}-3-methylbutyramide, 2-(1,1-dimethylethoxycarbonylamino)-N-{2-[3-methoxy-4-(4-chlorophenylprop-2-ynyloxy)-phenyl]-ethyl}-3-methylbutyramide, 2-(3,4-dichloro-phenyl)-N-[2-(3-methoxy-4-prop-2-ynyloxy-phenyl)-ethyl]-2-methoximino-acetamide, 2-(4-chloro-phenyl)-N-[2-(3-methoxy-4-prop-2-ynyloxy-phenyl)-ethyl-]-2-methoximino-acetamide, 2-(4-methyl-phenyl)-N-[2-(3-methoxy-4-prop-2-ynyloxy-phenyl)-ethyl]-2-methoximino-acetamide, and 2-(4-bromo-phenyl)-N-[2-(3-methoxy-4-prop-2-ynyloxy-phenyl)-ethyl]-2-methoximino-acetamide.

4. A compound of formula I according to claim 1 selected from the group consisting of 2-(4-chloro-phenyl)-2-hydroxy-N-[(R)2-(3-methoxy-4-prop-2-ynyloxy-phenyl)-propyl]-acetamide, 2-(4-chloro-phenyl)-2-hydroxy-N-[(S)2-(3-methoxy-4-prop-2-ynyloxy-phenyl)-propyl]-acetamide, 2-(4-chloro-2-nitro-phenyl)-2-hydroxy-N-[2-(3-methoxy4-prop-2-ynyloxy-phenyl)-ethyl]-acetamide, 2-(4-ethyl-phenyl)-2-hydroxy-N-[2-(3-methoxy-4-prop-2-ynyloxy-phenyl)-ethyl]-acetamide, 2-(4-trifluoromethyl-phenyl)-2-hydroxy-N-[2-(3-methoxy-4-prop-2-ynyloxy-phenyl)-ethyl]-acetamide, 2-(4-methyl-phenyl)-2-hydroxy-N-[2-(3-methoxy-4-prop-2-ynyloxy-phenyl)-ethyl]-acetamide, 2-(4-chloro-phenyl)-2-hydroxy-N-[2-(3-methoxy-4-pent-2-ynyloxy-phenyl)-ethyl]-acetamide, 2-(4-bromo-phenyl)-2-hydroxy-N-[2-(3-methoxy-4-pent-2-ynyloxy-phenyl)-ethyl]-acetamide, 2-(4-methyl-phenyl)-2-hydroxy-N-[2-(3-methoxy-4-pent-2-ynyloxy-phenyl)-ethyl]-acetamide, 2-(4-trifluoromethyl-phenyl)-2-hydroxy-N-[2-(3-methoxy-4-pent-2-ynyloxy-pheny)-ethyl]-acetamide, 2-(4-chloro-phenyl)-2-hydroxy-N-[2-(3-methoxy-4-hex-2-ynyloxy-phenyl)-ethyl]-acetamide, 2-(4-bromo-phenyl)-2-hydroxy-N-[2-(3-methoxy-4-hex-2-ynyloxy-phenyl)-ethyl]-acetamide, 2-(4-methyl-phenyl)-2-hydroxy-N-[2-(3-methoxy-4-hex-2-ynyloxy-phenyl)-ethyl]-acetamide, 2-(3,4-dichloro-phenyl)-2-hydroxy-N-[2-(3-methoxy-4-hex-2-ynyloxy-phenyl)-ethyl]-acetamide, 2-naphthyl-2-hydroxy-N-[2-(3-methoxy-4-hex-2-ynyloxy-phenyl)-ethyl]-acetamide, 2-(4-trifluoromethyl-phenyl)-2-hydroxy-N-[2-(3-methoxy-4-hex-2-ynyloxy-phenyl)-ethyl]-acetamide, 2-(4-biphenyl)-2-hydroxy-N-[2-(3-methoxy-4-prop-2-ynyloxy-phenyl)-ethyl]-acetamide, 2-(4-bromo-phenyl)-2-methyloxalyloxy-N-[2-(3-methoxy-4-prop-2-ynyloxy-phenyl)-ethyl]-acetamide, 2-(4-chloro-phenyl)-2-hydroxy-2-(prop-2-ynyl)-N-[2-(3-methoxy-4-prop-2-ynyloxy-phenyl)-ethyl]-acetamide, 2-(3,4-dichloro-phenyl)-N-[2-(3-methoxy4-pent-2-ynyloxy-phenyl)-ethyl]-2-oxo-acetamide, 2-(4-chloro-phenyl)-N-[2-(3-methoxy-4-prop-2-ynyloxy-phenyl)-ethyl]-2-methoxyimino-acetamide, 2-(4-methyl-phenyl)-N-[2-(3-methoxy-4-prop-2-ynyloxy-phenyl)-ethyl]-2-methoxyimino-acetamide, and 2-(3,4-dichloro-phenyl)-N-[2-(3-methoxy-4-prop-2-ynyloxy-phenyl)-ethyl]-2-methoxyimino-acetamide.

5. A process for the preparation of a compound of formula I according to claim 1, which comprises reacting a) an acid of formula II or a carboxy-activated derivative of an acid of formula II

 (II)

wherein $R_9$ is as defined for formula I is reacted with an amine of formula III

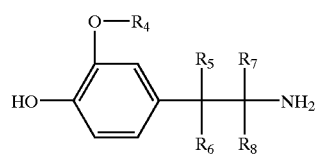 (III)

wherein $R_4$, $R_5$, $R_6$, $R_7$ and $R_8$ are as defined for formula I and reacting the intermediate phenol of formula IV

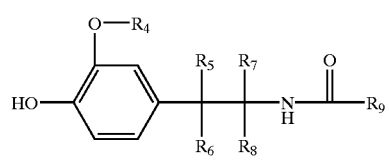 (IV)

wherein $R_4$, $R_5$, $R_6$, $R_7$, $R_8$ and $R_9$ are as defined for formula I with a compound of formula V

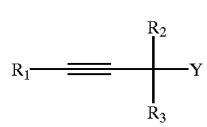 (V)

wherein $R_1$, $R_2$ and $R_3$ are as defined for formula I and wherein Y is a leaving group; or b) alkylating a compound of formula VI

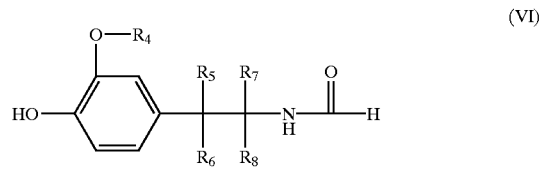 (VI)

wherein $R_4$, $R_5$, $R_6$, $R_7$ and $R_8$ are as defined for formula I with a compound of formula V

 (V)

wherein $R_1$, $R_2$ and $R_3$ are as defined for formula I and wherein Y is a leaving group and dehydrating the intermediate compound of formula VII

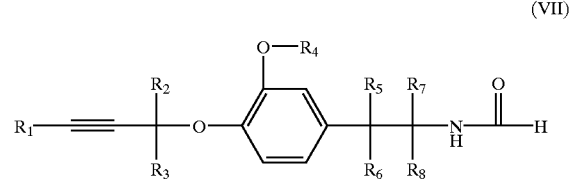 (VII)

wherein $R_1$, $R_2$, $R_3$, $R_4$, $R_5$, $R_6$, $R_7$ and $R_8$ are as defined for formula I to an isocyanide of formula VIII

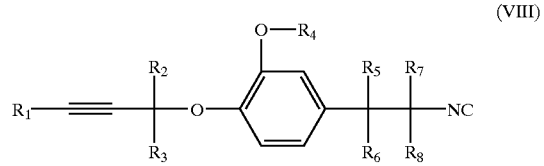 (VIII)

wherein $R_1$, $R_2$, $R_3$, $R_4$, $R_5$, $R_6$, $R_7$ and $R_8$ are as defined for formula I which then is reacted with an aldehyde or ketone of formula IX

 (IX)

wherein $R_{10}$ and $R_{11}$ are as defined for formula I in the presence of a carboxylic acid

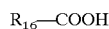

wherein $R_{16}$ is hydrogen or lower alkyl to give a O-acyl-α-hydroxy amide of subformula Ia (Ia)

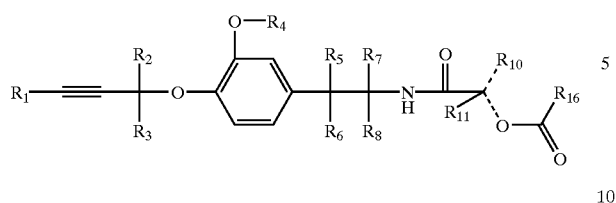

wherein $R_1$, $R_2$, $R_3$, $R_4$, $R_5$, $R_6$, $R_7$, $R_8$, $R_{10}$ and $R_{11}$ are as defined for formula I.

6. A composition for controlling and protecting against phytopathogenic microorganisms, comprising a compound of formula I according to claim 1 as active ingredient together with a suitable carrier.

7. A method of controlling and preventing an infestation of crop plants by phytopathogenic microorganisms, which comprises the application of a compound of formula I according to claim 1 as active ingredient to the plant, to parts of plants or to the locus thereof.

8. A method according to claim 7, wherein the phytopathogenic microorganisms are fungal organisms.

9. A compound according to claim 1 wherein $R_1$ is hydrogen, alkyl, cycloalkyl, phenyl or naphthyl; phenyl and naphthyl being optionally substituted by substituents selected from the group consisting of alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; or alkynyloxycarbonyl; and $R_4$ is alkyl; and $R_{10}$ is aryl or heteroaryl, each optionally substituted by substituents selected from to group consisting of alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl; and Z is hydrogen or —CO—$R_{16}$ wherein $R_{16}$ is alkyl; and $R_{15}$ is alkyl, alkenyl, alkynyl; aryl or aryl-alkyl wherein aryl and aryl-alkyl are each optionally substituted by substituents selected from the group consisting of alkyl, alkenyl, alkynyl, cycloalkyl, cycloalkyl-alkyl, phenyl and phenylalkyl, where all these groups may be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl and alkynyloxycarbonyl.

10. A compound of formula I according to claim 1 wherein $R_1$ is hydrogen, $C_1$–$C_8$-alkyl, $C_3$–$C_8$-cycloalkyl, phenyl or naphthyl; phenyl and naphthyl being optionally substituted by one to three substituents selected from the group consisting of $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl; and $R_2$, $R_3$, $R_5$, $R_6$, and $R_7$ are hydrogen; and $R_4$ and $R_8$ are independently $C_1$–$C_6$-alkyl; and $R_{10}$ is phenyl, naphthyl, 1,3-biphenyl or 1,4-biphenyl, each optionally substituted by one to three substituents selected from the group consisting of $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_8$-haloalkylthio, $C_1$–$C_8$-alkylsulfonyl, halogen, cyano, nitro and $C_1$–$C_8$-alkoxycarbonyl; and $R_{11}$ is hydrogen or $C_1$–$C_4$-alkyl; and Z is hydrogen or acetyl; and $R_{12}$ is hydrogen, $C_1$–$C_6$-alkyl, $C_3$–$C_6$-alkenyl or $C_3$–$C_6$-alkynyl; and $R_{13}$ is hydrogen or $C_1$–$C_4$-alkyl; and $R_{14}$ is $C_1$–$C_6$-alkyl or $C_3$–$C_7$-cycloalkyl; and $R_{15}$ is $C_1$–$C_8$-alkyl, $C_3$–$C_8$-alkenyl, $C_3$–$C_8$-alkynyl; phenyl or benzyl wherein the phenyl and benzyl is optionally substituted by one to three substituents selected from the group consisting of $C_1$–$C_8$-alkyl, $C_2$–$C_8$-alkenyl, $C_2$–$C_8$-alkynyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, $C_1$–$C_8$-alkylsulfonyl, halogen, cyano, nitro and $C_1$–$C_8$-alkoxycarbonyl.

11. A compound of formula I according to claim 1 wherein $R_1$ is hydrogen, $C_1$–$C_8$-alkyl, phenyl optionally substituted by one to three substituents selected from the group consisting of $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen, cyano, nitro and $C_1$–$C_8$-alkoxycarbonyl; and $R_2$, $R_3$, $R_5$, $R_6$, and $R_7$ are hydrogen; and $R_4$ and $R_8$ are each independently methyl or ethyl; and $R_{10}$ is phenyl, naphthyl, 1,3-biphenyl or 1,4-biphenyl, each optionally substituted by one to three substituents selected from the group consisting of $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen, cyano, nitro and $C_1$–$C_8$-alkoxycarbonyl; and $R_{11}$, Z and $R_{13}$ are each hydrogen; and $R_{12}$ is hydrogen or $C_1$–$C_3$-alkyl; and $R_{14}$ is $C_2$–$C_5$-alkyl or $C_3$–$C_7$-cycloalkyl; and $R_{15}$ is $C_3$–$C_6$-alkyl, $C_3$–$C_6$-alkenyl or phenyl optionally substituted by one to three substituents selected from the group consisting of $C_1$–$C_8$-alkyl, $C_1$–$C_8$-haloalkyl, $C_1$–$C_8$-alkoxy, $C_1$–$C_8$-haloalkoxy, $C_1$–$C_8$-alkylthio, $C_1$–$C_8$-haloalkylthio, halogen and cyano.

12. A process for the preparation of a compound of formula I according to claim 8, wherein the compound of subformula Ia is hydrolyzed to an α-hydroxy amide of subformula Ib

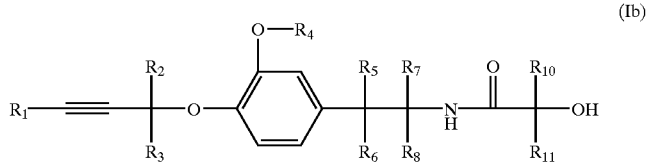
(Ib)

wherein $R_1$, $R_2$, $R_3$, $R_4$, $R_5$, $R_6$, $R_7$, $R_8$, $R_{10}$ and $R_{11}$ are as defined for formula I.

13. A process for the preparation of a compound of formula I according to claim 12, wherein the compound of subformula Ib is oxidized with an organic oxidizing agent or an inorganic oxidizing agent to yield the compound of subformula Ic

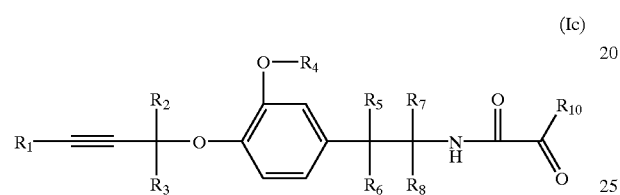
(Ic)

wherein $R_1$, $R_2$, $R_3$, $R_4$, $R_5$, $R_6$, $R_7$, $R_8$ and $R_{10}$ are as defined for formula I.

14. A process for the preparation of a compound of formula I according to claim 13, wherein the compound of subformula Ic is reacted with

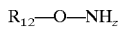

wherein $R_{12}$ is as defined above to give a compound of subformula Id

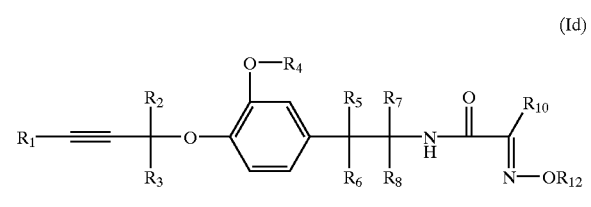
(Id)

wherein $R_1$, $R_2$, $R_3$, $R_4$, $R_5$, $R_6$, $R_7$, $R_8$, $R_{10}$ and $R_{12}$ are as defined above.

* * * * *